(12) United States Patent
Morita

(10) Patent No.: US 10,737,295 B2
(45) Date of Patent: Aug. 11, 2020

(54) PIEZOELECTRIC ELEMENT, METHOD FOR PRODUCING THE SAME, ULTRASOUND PROBE, AND ULTRASOUND IMAGING APPARATUS

(71) Applicant: Konica Minolta, Inc., Tokyo (JP)

(72) Inventor: Kiyokazu Morita, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 450 days.

(21) Appl. No.: 15/863,335

(22) Filed: Jan. 5, 2018

(65) Prior Publication Data

US 2018/0193879 A1 Jul. 12, 2018

(30) Foreign Application Priority Data

Jan. 6, 2017 (JP) .................................. 2017-001238

(51) Int. Cl.
| | |
|---|---|
| *H01L 41/02* | (2006.01) |
| *H01L 41/18* | (2006.01) |
| *B06B 1/06* | (2006.01) |
| *A61B 9/00* | (2006.01) |
| *C08J 3/24* | (2006.01) |
| *H01L 41/277* | (2013.01) |
| *A61B 8/00* | (2006.01) |
| *H01L 41/37* | (2013.01) |

(Continued)

(52) U.S. Cl.
CPC .......... *B06B 1/0629* (2013.01); *A61B 8/4405* (2013.01); *A61B 8/4444* (2013.01); *C08J 3/24* (2013.01); *H01L 41/18* (2013.01); *H01L 41/183* (2013.01); *H01L 41/277* (2013.01); *H01L 41/37* (2013.01); *C08J 2363/00* (2013.01); *C08J 2483/04* (2013.01); *G01S 7/52079* (2013.01); *H01L 41/0825* (2013.01)

(58) Field of Classification Search
CPC ... B06B 1/0629; A61B 8/4405; A61B 8/4444; C08J 3/24; C08J 2363/00; C08J 2483/04; H01L 41/18; H01L 41/183; H01L 41/277; H01L 41/37; H01L 41/0825; G01S 7/52079
USPC ........................................................ 310/334
See application file for complete search history.

(56) References Cited

U.S. PATENT DOCUMENTS

| | | | | |
|---|---|---|---|---|
| 5,691,960 | A | * 11/1997 | Gentilman | ............ B06B 1/0629 367/155 |
| 2005/0001517 | A1 | * 1/2005 | Yogeswaren | ........ G10K 11/002 310/334 |

(Continued)

FOREIGN PATENT DOCUMENTS

| | | |
|---|---|---|
| JP | H06-224487 A | 8/1994 |
| JP | 2015-015343 A | 1/2015 |
| JP | 2016-025611 A | 2/2016 |

*Primary Examiner* — Thomas M Dougherty
(74) *Attorney, Agent, or Firm* — Osha Liang LLP

(57) ABSTRACT

The piezoelectric element includes a piezoelectric composite including a plurality of piezoelectrics and a reaction product, and an electrode pair. The plurality of piezoelectrics is disposed in alignment at an interval of 1 to 10 μm. The aspect ratio of each of the piezoelectrics is 5 or higher. The reaction product is a reaction product of a crosslinkable epoxy resin composition containing an elastomer component, a crosslinkable epoxy resin, and a crosslinking agent. One or each of a number of epoxy groups per molecule of the crosslinkable epoxy resin and a crosslinking value of the crosslinking agent is 3 or more.

12 Claims, 8 Drawing Sheets

(51) Int. Cl.
*H01L 41/08* (2006.01)
*G01S 7/52* (2006.01)

(56) References Cited

U.S. PATENT DOCUMENTS

| | | | |
|---|---|---|---|
| 2011/0074249 A1* | 3/2011 | Sakashita | C08K 3/22 |
| | | | 310/339 |
| 2015/0311424 A1* | 10/2015 | Krohn | H01L 41/37 |
| | | | 310/322 |
| 2018/0083183 A1* | 3/2018 | Bella | H01L 41/183 |

* cited by examiner

PIEZOELECTRIC ELEMENT, METHOD FOR PRODUCING THE SAME, ULTRASOUND PROBE, AND ULTRASOUND IMAGING APPARATUS

CROSS REFERENCE TO RELATED APPLICATIONS

Japanese Patent Application No. 2017-001238 filed on Jan. 6, 2017, including description, claims, drawings, and abstract the entire disclosure is incorporated herein by reference in its entirety.

BACKGROUND

Technological Field

The present invention relates to a piezoelectric element, a method for producing the piezoelectric element, an ultrasound probe, and an ultrasound imaging apparatus.

Description of Related Art

An ultrasound imaging apparatus utilized in the medical field includes an ultrasound probe including a piezoelectric element. Known as the piezoelectric element is, for example, a piezoelectric element including a piezoelectric composite including a plurality of piezoelectrics and a reaction product (cured product) of a crosslinkable epoxy resin composition, the reaction product filling a gap of the plurality of piezoelectrics; and an electrode pair that applies a voltage to the piezoelectric composite (e.g., see Japanese Patent Application Laid-Open Nos. 6-224487 and 2015-015343).

If the aspect ratio of each piezoelectric of such a conventional piezoelectric element is set high and the interval of the plurality of piezoelectrics is set excessively small, interaction may take place between adjacent piezoelectrics to lower the electromechanical coupling factor of the piezoelectric element.

To prevent the lowering of the electromechanical coupling factor due to the interaction between adjacent piezoelectrics, a piezoelectric element including a piezoelectric composite including the reaction product containing a flexible, modified-silicone rubber particle is known (e.g., see Japanese Patent Application Laid-Open No. 2016-025611).

In the case that the reaction product contains flexible elastomer such as silicone rubber, however, adhesion between the piezoelectric and the reaction product may be insufficient. If the adhesion is insufficient, the reaction product may be peeled off from the piezoelectric composite in production of a piezoelectric element, and thus result in insufficient processability.

In the case that the reaction product contains flexible elastomer such as silicone rubber and the electrode pair is disposed directly on both end surfaces of the reaction product, the adhesion between the electrode pair and the reaction product may be insufficient to cause peeling-off of the electrode pair from the piezoelectric composite.

Further, the epoxy resin may lower the sensitivity of an ultrasound probe through swelling caused by an agent such as an antiseptic solution and fatty acid contained in the human skin.

As described above, conventional piezoelectric elements have not achieved a satisfactory level for all of the electromechanical coupling factor, the processability of the piezoelectric composite, the adhesion between the reaction product and the electrode pair, and the chemical durability.

SUMMARY

One or more embodiments of the present invention provide a piezoelectric element which is capable of preventing interaction to take place between adjacent piezoelectrics and excellent in processability and durability, and has excellent adhesion between the reaction product and the electrode pair directly disposed on the reaction product.

Further, one or more embodiments of the present invention provide an ultrasound probe keeping a high sensitivity for a long period of time.

Further still, one or more embodiments of the present invention provide an ultrasound imaging apparatus capable of providing an ultrasonic image of a subject with high spatial resolution for a long period of time.

A piezoelectric element according to one or more embodiments of the invention includes a piezoelectric composite and an electrode pair that is disposed to face each other with the piezoelectric composite sandwiched therebetween and applies a voltage to the piezoelectric composite. The piezoelectric composite includes: a plurality of piezoelectrics disposed in alignment along a direction perpendicular to the facing direction of the electrode pair at an interval of 1 to 10 μm, wherein the ratio of the length in the facing direction to the length in the alignment direction in each of the piezoelectrics is 5 or higher; and a reaction product of a crosslinkable epoxy resin composition containing an elastomer component, a crosslinkable epoxy resin, and a crosslinking agent, the reaction product filling a gap of the plurality of piezoelectrics. One or each of the number of epoxy groups possessed by the crosslinkable epoxy resin per molecule and the crosslinking value of the crosslinking agent is 3 or more.

The ultrasound probe according to one or more embodiments of the present invention includes the piezoelectric element.

The ultrasound imaging apparatus according to one or more embodiments of the present invention includes the ultrasound probe.

A method for producing a piezoelectric element according to one or more embodiments of the present invention includes: filling a gap of a plurality of piezoelectrics disposed in alignment at an interval of 1 to 10 μm, wherein the ratio of the length in a height direction to the length in the alignment direction in each of the piezoelectrics is 5 or higher, with a crosslinkable epoxy resin composition containing an elastomer component, a crosslinkable epoxy resin, and a crosslinking agent, wherein one or each of the number of epoxy groups possessed by the crosslinkable epoxy resin per molecule and the crosslinking value of the crosslinking agent is 3 or more; obtaining a piezoelectric composite through reacting an epoxy group of the crosslinkable epoxy resin and a crosslinkable functional group of the crosslinking agent to form a reaction product of the crosslinkable epoxy resin composition; and forming an electrode pair on both end surfaces of the piezoelectric composite in the height direction, wherein the electrode pair is disposed to face each other and applies a voltage to the piezoelectric composite.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION

Hereinafter, embodiments of the present invention will be described with reference to the drawings. However, the scope of the invention is not limited to the disclosed embodiments.

[Configuration of Piezoelectric Element]

Figure 1:
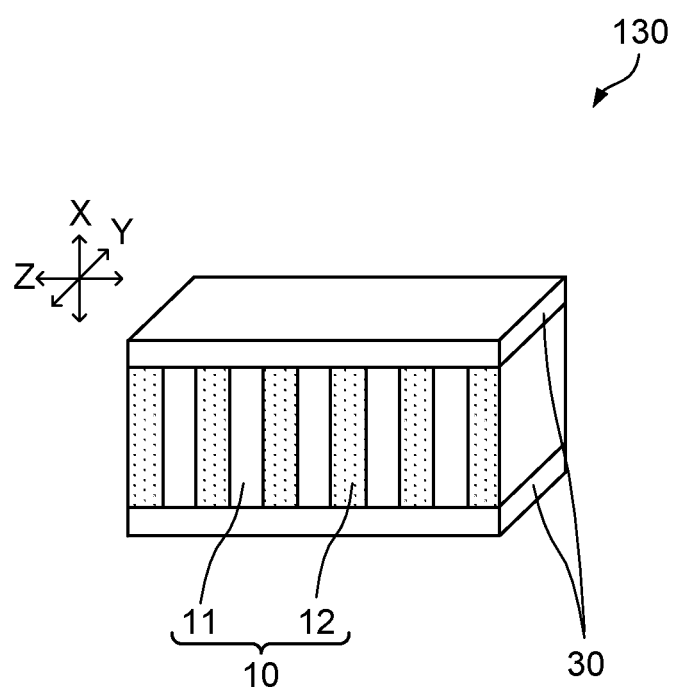
FIG. 1 is a perspective view illustrating one example of the configuration of a piezoelectric element according to one or more embodiments of the present invention.

FIG. 1 is a perspective view illustrating one example of the configuration of piezoelectric element 130 according to one or more embodiments of the present invention. Piezoelectric element 130 according to one or more embodiments includes piezoelectric composite 10 and electrode pair 30 that is disposed to face each other and applies a voltage to piezoelectric composite 10. In FIG. 1, the X direction is defined as the height direction of piezoelectric 11, the Y direction as the length direction of piezoelectric 11, and the Z direction as the thickness direction of piezoelectric 11. The X direction coincides with the facing direction of electrode pair 30. The Z direction coincides with the alignment direction of piezoelectrics 11. The height direction of piezoelectric 11 (X direction) is a direction intersecting a plane lying along the alignment direction of piezoelectrics 11 (YZ plane). Each of the X direction, the Y direction, and the Z direction is perpendicular to the other two directions.

(Piezoelectric Composite)

Piezoelectric composite 10 according to one or more embodiments includes a plurality of piezoelectrics 11 and reaction products 12 of a crosslinkable epoxy resin composition. In one or more embodiments, the plurality of piezoelectrics 11 and the plurality of reaction products 12 are alternately disposed in alignment along the Z direction. The plurality of piezoelectrics 11 is disposed in alignment at intervals via reaction products 12 along the Z direction.

Herein, "piezoelectric composite" refers to a piezoelectric member including a plurality of miniaturized piezoelectrics and a reaction product (cured product) of a crosslinkable epoxy resin composition filling a gap between adjacent piezoelectrics.

The interval between adjacent piezoelectrics 11 in each direction (Z direction and Y direction) perpendicular to the facing direction (X direction) is 1 to 10 µm. If the interval is excessively small, production of piezoelectric element 130 is difficult, and interaction may take place between adjacent piezoelectrics 11 to impart an insufficient electromechanical coupling factor to piezoelectric element 130. If the interval is excessively large, the sensitivity to ultrasound may be insufficient. From these viewpoints, the interval is preferably 2 to 8 µm, and more preferably 3 to 6 µm.

The shape of each piezoelectric 11 can be appropriately changed in accordance with the shape of piezoelectric composite 10. Examples of the shape of each piezoelectric 11 include a column and a plate. The shape of each piezoelectric 11 in one or more embodiments is a plate.

The ratio of the length in the facing direction (X direction) to the length in the alignment direction (Z direction) (hereinafter, also referred to as "aspect ratio") in each piezoelectric 11 is 5 or higher. If the aspect ratio is excessively low, larger unnecessary vibration is caused to piezoelectric 11 in the directions other than the X direction, and the vibration is transmitted to adjacent piezoelectrics 11, resulting in an insufficient electromechanical coupling factor in some cases. The upper limit of the aspect ratio may be any value which provides an intended electromechanical coupling factor, and the upper limit is, for example, 100. From these viewpoints, the aspect ratio is preferably 10 to 20.

In the case that each piezoelectric 11 is a plate, similarly, the ratio of the length in the facing direction (X direction) to the length in the length direction (Y direction) in each piezoelectric 11 is preferably 5 or higher.

The material of piezoelectric 11 may be any known piezoelectric material applicable as a material for piezoelectric 11. Examples of the material of piezoelectric 11 include lead zirconate titanate (PZT), lead magnesium niobate-lead titanate (PMN-PT), lead zinc niobate-lead titanate (PZN-PT), lead scandium niobate-lead titanate (PSN-PT), lead indium niobate-lead titanate (PIN-PT), lead indium niobate-lead magnesium niobate-lead titanate (PIN-PMN-PT), quantz, lithium niobate ($LiNbO_3$), barium titanate ($BaTiO_3$), and lithium tantalate ($TaTiO_3$).

The size of each piezoelectric 11 can be appropriately changed in accordance with the size of piezoelectric composite 10, the intended dielectric constant, the frequency of ultrasound, the resonance frequency of the material of piezoelectric 11, the focus distance, and so on. For example, the length of each piezoelectric 11 in the facing direction is preferably 50 to 600 mm. For example, the minimum value of the length of each piezoelectric 11 in the direction coincident with the alignment direction of piezoelectrics 11 and perpendicular to the X direction (the length of each piezoelectric 11 in the Z direction) is preferably 0.002 to 30 mm, and more preferably 0.005 to 20 mm. The maximum value of the length of each piezoelectric 11 in the direction coincident with the alignment direction of piezoelectrics 11 and perpendicular to the X direction (the length of each piezoelectric 11 in the Y direction) is preferably 2 to 300 µm, and more preferably 5 to 200 µm.

Each reaction product 12 fixes adjacent piezoelectrics 11 at a given interval. Gaps of the plurality of piezoelectrics 11 are each filled with reaction product 12. Reaction product 12 is a reaction product of a crosslinkable epoxy resin composition containing an elastomer component, a crosslinkable epoxy resin, and a crosslinking agent. More specifically, reaction product 12 is a reaction product resulting from reaction between an epoxy group of a crosslinkable epoxy resin and a crosslinkable functional group of a crosslinking agent in a crosslinkable epoxy resin composition.

Now, the components constituting reaction product 12 will be described. In the crosslinkable epoxy resin composition, one or each of the number of epoxy groups possessed by the crosslinkable epoxy resin per molecule and the crosslinking value of the crosslinking agent is 3 or more.

The elastomer component is a resin or rubber having elasticity. The elastomer component contained in reaction product 12 imparts elasticity to reaction product 12 and lowering of the electromechanical coupling factor due to interaction between adjacent piezoelectrics 11 can be prevented. The elastomer component may be contained in reaction product 12 as an elastomer particle, or may be contained in reaction product 12 as a backbone component of the crosslinkable epoxy resin.

The elastomer component is preferably contained phase-separated to some extent in reaction product 12. Thereby, an intended elasticity can be imparted to reaction product 12. From this viewpoint, it is preferred that the elastomer component be contained in reaction product 12 as an elastomer particle. In the case that the elastomer component is an elastomer particle, the number average primary particle size of the elastomer particle is preferably 3 μm, and more preferably 1 μm. More specifically, the number average primary particle size of the elastomer particle is preferably 0.05 to 3 μm, and more preferably 0.1 to 1 μm. The number average primary particle size of the elastomer particle can be appropriately adjusted in accordance with the interval between adjacent piezoelectrics 11. The number average primary particle size of the elastomer particle can be measured, for example, through electron microscopy for reaction product 12.

The elastomer constituting the elastomer particle can be appropriately selected in accordance with intended elasticity. Examples of the elastomer constituting the elastomer particle include silicone rubber, acrylic rubber, urethane rubber, nitrile rubber, and butadiene rubber. To allow the elastomer component to be moderately phase-separated, it is preferred that the elastomer constituting the elastomer particle be silicone elastomer.

In the case that the elastomer component is contained in reaction product 12 as a backbone component of the crosslinkable epoxy resin, the number average molecular weight of the elastomer backbone part of the crosslinkable epoxy resin is preferably 50 to 10,000. If the number average molecular weight is excessively low, intended elasticity is not imparted to reaction product 12 in some cases. If the number average molecular weight is excessively high, intended processability, adhesion, and durability are not achieved in some cases. From the viewpoint of the flexibility and adhesion of reaction product 12, the number average molecular weight of the elastomer backbone part is more preferably 100 to 2,000. The glass transition temperature of the elastomer backbone part is, for example, 25° C. or lower.

The elastomer constituting the elastomer backbone part can be appropriately selected in accordance with intended elasticity. Preferred for the elastomer constituting the elastomer backbone part are silicone rubber, butadiene rubber, propylene oxide, polyethylene oxide, acrylic rubber, and hydrogenated products of them. More preferred for the elastomer constituting the elastomer backbone part among them are silicone rubber, butadiene rubber, and hydrogenated products thereof.

The content of the elastomer component in reaction product 12 is preferably 5 to 50 parts by weight, and more preferably 20 to 40 parts by weight, with respect to 100 parts by weight of reaction product 12. If the content is excessively low, the electromechanical coupling factor may be insufficient. If the content is excessively high, the hardness of reaction product 12 may be lowered to cause insufficient adhesion between reaction product 12 and piezoelectric 11 or between reaction product 12 and electrode pair 30, or result in piezoelectric element 130 having insufficient durability. The content can be appropriately adjusted in accordance with the type of the elastomer component.

The crosslinkable epoxy resin has an epoxy group. As described above, the crosslinkable epoxy resin composition contains one or both of the trifunctional or higher-functional (the number of epoxy groups per molecule is three or more) crosslinkable epoxy resin and the trivalent or higher-valent crosslinking agent. In the case that the crosslinkable epoxy resin is a difunctional or monofunctional crosslinkable epoxy resin, a known crosslinkable epoxy resin can be used for it.

The epoxy equivalent of the trifunctional or higher-functional crosslinkable epoxy resin is preferably 80 to 6,000 g/mol, more preferably 100 to 5,000 g/mol, and even more preferably 150 to 3,000 g/mol. If the epoxy equivalent is excessively low, the number of epoxy groups per unit volume is excessively large, and the number of epoxy groups remaining unreacted in reaction product 12 tends to be larger. As a result, the remaining epoxy groups decompose or react to change the physical properties of reaction product 12 over time, and the durability of piezoelectric element 130 may be lowered. If the epoxy equivalent is excessively high, on the other hand, the number of epoxy groups per unit volume may be insufficient. As a result, reaction product 12 may have lower crosslinking density and thus have insufficient strength, and hence intended processability, adhesion, and durability are not achieved in some cases.

The weight average molecular weight of the trifunctional or higher-functional crosslinkable epoxy resin is preferably 150 to 50,000, and more preferably 200 to 30,000. If the weight average molecular weight is excessively low, the volatility of the trifunctional or higher-functional crosslinkable epoxy resin is higher, and the crosslinkable epoxy resin volatilizes from the crosslinkable epoxy resin composition to result in reaction product 12 having insufficient strength, and hence intended processability, adhesion, and durability are not achieved in some cases. If the weight average molecular weight is excessively high, the solubility of the crosslinkable epoxy resin is lowered, and it is difficult to allow the crosslinkable epoxy resin composition to contain an adequate quantity of the crosslinkable epoxy resin, and as a result insufficient strength is imparted to reaction product 12, and hence intended processability, adhesion, and durability are not achieved in some cases. In addition, if the weight average molecular weight is excessively large, the viscosity of the crosslinkable epoxy resin composition is higher, and it is difficult in some cases to fill a gap of piezoelectrics 11 each having a high aspect ratio with the crosslinkable epoxy resin composition.

The type of the crosslinkable epoxy resin can be appropriately selected in accordance with the reactivity of the crosslinkable epoxy resin, the storage stability of the crosslinkable epoxy resin composition, chemical resistance, and the type of the crosslinking agent. Examples of the type of the crosslinkable epoxy resin include glycidyl ether epoxy resin, glycidyl ester epoxy resin, glycidylamine epoxy resin, phenol novolac epoxy resin, cresol novolac epoxy resin, bisphenol A epoxy resin, bisphenol F epoxy resin, biphenyl aralkyl epoxy resin, cyanuric acid epoxy resin, alicyclic epoxy resin, and long-chain aliphatic epoxy resin. To enhance the storage stability of the crosslinkable epoxy resin composition, the type of the crosslinkable epoxy resin is preferably glycidyl ether epoxy resin or glycidyl ester epoxy resin.

The glycidyl ether epoxy resin preferably has the same structure as a reaction product of epichlorohydrin and a compound represented by formula (1). More specifically, the glycidyl ether epoxy resin preferably has the same structure as a reaction product obtained through ring closure of chlorohydrin with a base such as sodium hydroxide, the chlorohydrin generated from addition reaction between epichlorohydrin and the hydroxy groups of the compound represented by formula (1). A part of epoxy groups possessed by the glycidyl ether epoxy resin may be ring-opened.

$$R_1(OH)_m \quad (1)$$

In formula (1), m is an integer of 3 to 30, and $R_1$ is a $C_{2-200}$ hydrocarbon group, a $C_{2-300}$ hydrocarbon group having an oxy group, or a $C_{3-50}$ hydrocarbon group having an isocyanurate ring. From the viewpoint of solubility, it is preferred that m be 3 to 20 and $R_1$ be a $C_{2-150}$ hydrocarbon group, or that m be 2 to 20 and $R_1$ be a $C_{2-150}$ hydrocarbon group having an oxy group.

Examples of compounds in which $R_1$ is a $C_{2-150}$ hydrocarbon group among compounds represented by formula (1) include glycerin, pentaerythritol, phenol novolac, cresol novolac, trimethylolpropane, and bisphenol A.

Examples of compounds in which $R_1$ is a $C_{2-150}$ hydrocarbon group having an oxy group among compounds represented by formula (1) include dipentaerythritol.

The glycidyl ester epoxy resin preferably has the same structure as a reaction product of compounds having an epoxy group such as glycidyl (meth)acrylate, or a reaction product resulting from copolymerization reaction of such a compound and a $C_{4-25}$ alkyl (meth)acrylate (weight average molecular weight: 500 to 20,000). Herein, "(meth)acrylate" refers to one or both of acrylate and methacrylate.

The glycidyl ester epoxy resin preferably has the same structure as a reaction product of epichlorohydrin and a compound represented by formula (2). More specifically, the glycidyl ether epoxy resin preferably has the same structure as a reaction product obtained through ring closure of chlorohydrin with a base such as sodium hydroxide, the chlorohydrin generated from addition reaction between epichlorohydrin and the carboxy groups of the compound represented by formula (2). A part of epoxy groups possessed by the glycidyl ether epoxy resin may be ring-opened.

$$R_2(COOH)_n \quad (2)$$

In formula (2), n is an integer of 2 to 8, and $R_2$ is a $C_{2-20}$ hydrocarbon group, a $C_{2-30}$ hydrocarbon group having an oxy group, or a $C_{3-50}$ hydrocarbon group having an isocyanurate ring. From the viewpoint of solubility, it is preferred that n be 3 or 4 and $R_2$ be a $C_{2-10}$ hydrocarbon group, or that n be 3 to 6 and $R_2$ be a $C_{2-30}$ hydrocarbon group having an oxy group, or that n be 3 and $R_2$ be a $C_{9-50}$ hydrocarbon group having an isocyanurate ring.

Examples of compounds in which n is 3 or 4 and $R_2$ is a $C_{2-10}$ hydrocarbon group among compounds represented by formula (2) include trimellitic acid and pyromellitic acid.

Examples of compounds in which n is 3 to 6 and $R_2$ is a $C_{2-30}$ hydrocarbon group having an oxy group among compounds represented by formula (2) include a reaction product of pentaerythritol and mellitic anhydride.

Examples of compounds in which n is 3 and $R_2$ is a $C_{9-50}$ hydrocarbon group having an isocyanurate ring among compounds represented by formula (2) include 1,3,5-tris(2-carboxyethyl) isocyanurate.

Examples of the phenol novolac epoxy resin and the cresol novolac epoxy resin include compounds represented by general formula (1).

[Chemical Formula 1]

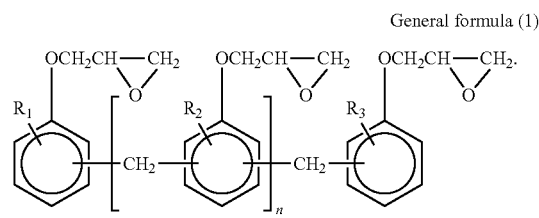

General formula (1)

In general formula (1), n is an integer of 1 or more, and $R_1$, $R_2$, and $R_3$ are each a hydrogen atom or a methyl group.

Examples of the biphenyl aralkyl epoxy resin include compounds represented by formula (3).

[Chemical Formula 2]

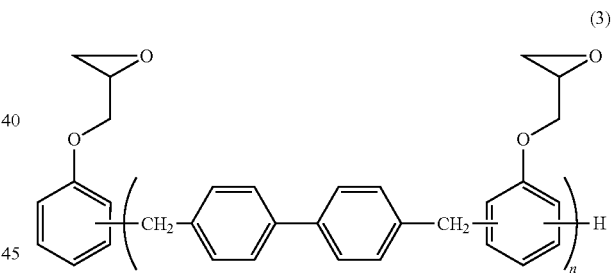

(3)

In formula (3), n is an integer of 1 to 10.

Examples of the cyanuric acid epoxy resin include compounds represented by general formula (2).

[Chemical Formula 3]

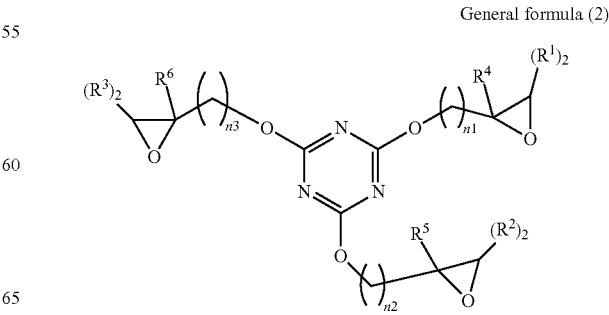

General formula (2)

In general formula (2), n1, n2, and n3 are each an integer of 2 to 6, and $R^1$, $R^2$, $R^3$, $R^4$, $R^5$, and $R^6$ are each independently a hydrogen atom or a $C_{1-10}$ alkyl group. Examples of the alkyl group include a methyl group, an ethyl group, an n-propyl group, an i-propyl group, a cyclopropyl group, an n-butyl group, an i-butyl group, an s-butyl group, a t-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-butyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Specific examples of compounds represented by general formula (2) include compounds represented by formulas (2-1) to (2-5).

[Chemical Formula 4]

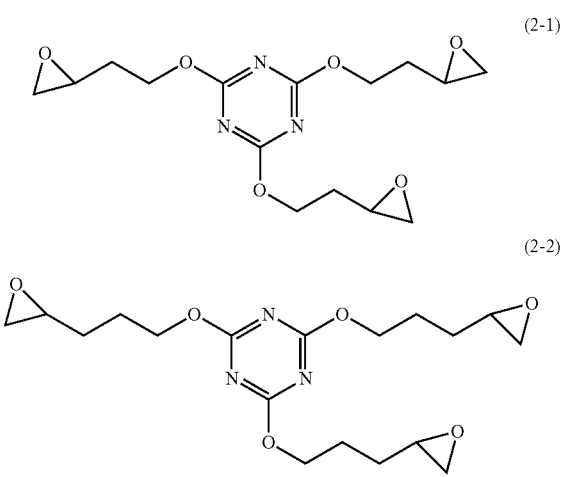

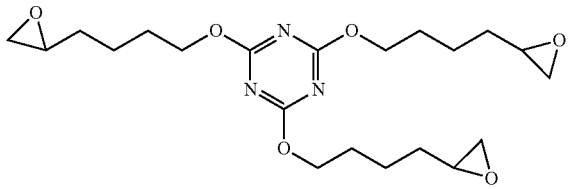

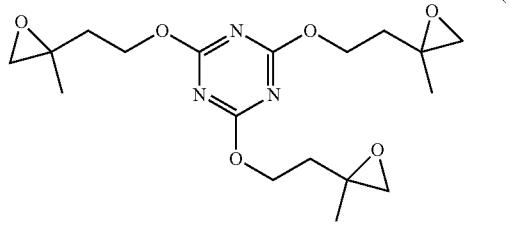

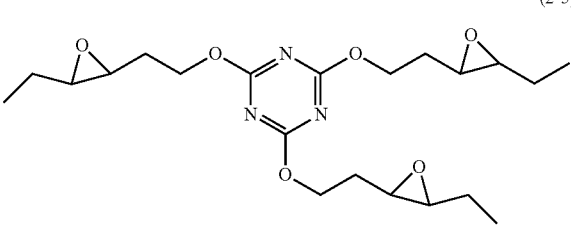

In order to enhance the processability, adhesion, and durability, it is preferred for the crosslinkable epoxy resin to have an aromatic ring. This is because aromatic rings in reaction product 12 interact with each other to increase the crosslinking density of reaction product 12, and thereby sufficient strength is imparted to reaction product 12.

In order to enhance the processability, adhesion, and durability, it is preferred for the trifunctional or higher-functional crosslinkable epoxy resin to have a constitutional unit having an epoxy group. In other words, it is preferred that the crosslinkable epoxy resin be a trifunctional or higher-functional multimeric crosslinkable epoxy resin. This is because the crosslinking density of reaction product 12 in this case is higher than that in the case of a difunctional multimeric crosslinkable epoxy resin having an epoxy group only at each end, and thus sufficient strength is imparted to reaction product 12.

From the same viewpoint, it is also preferred for the trifunctional or higher-functional crosslinkable epoxy resin to have no constitutional unit. In other words, it is preferred that the crosslinkable epoxy resin be a trifunctional or higher-functional monomeric crosslinkable epoxy resin. This is because the crosslinking density of reaction product 12 in this case is higher than that in the case of a difunctional multimeric crosslinkable epoxy resin having an epoxy group only at each end, and thus sufficient strength is imparted to reaction product 12.

The crosslinkable epoxy resin may be synthesized or a commercially available product may be used for the crosslinkable epoxy resin. For example, the crosslinkable epoxy resin can be synthesized through oxidation of a compound having a double bond with a peroxide.

Examples of commercially available products of difunctional or monofunctional crosslinkable epoxy resin include jER152 (difunctional, "jER" is a registered trademark possessed by the manufacturer, omitted below), 154, and 180S manufactured by Mitsubishi Chemical Corporation.

Examples of commercially available products of the trifunctional or higher-functional crosslinkable epoxy resin include EPICLON N-740 ("EPICLON" is a registered trademark possessed by the manufacturer, omitted below), N-770, N-775, N-660, N-665, N-680, and N-695 manufactured by DIC Corporation; YDPN638, YDPN638P, YDCN701, YDCN702, YDCN703, and YDCN704 manufactured by TOHTO Chemical Industry Co., Ltd.; DEN431, DEN438, and DEN439 manufactured by The Dow Chemical Company; NC3000, NC3000-FH, NC3000-H, NC3000-L, and NC3100 manufactured by Nippon Kayaku Co., Ltd.; TECHMORE VG3101 (trifunctional, "TECHMORE" is a registered trademark possessed by the manufacturer) manufactured by Printec Corporation; TG-G (tetrafunctional) manufactured by SHIKOKU CHEMICALS CORPORATION; and TEPIC-UC (hexafunctional, "TEPIC" is a registered trademark possessed by the manufacturer), TEPIC-VL (trifunctional), TEPIC-L (trifunctional), TEPIC-FL (trifunctional), and TEPIC-PAS (trifunctional) manufactured by Nissan Chemical Industries, Ltd.

As described above, the elastomer component may be contained in reaction product 12 as an elastomer particle. In this case, examples of commercially available products of the crosslinkable epoxy resin containing the elastomer component as an elastomer particle include ACRYSET BPA328 (difunctional, "ACRYSET" is a registered trademark possessed by the manufacturer, omitted below) and BPF307 (difunctional) manufactured by NIPPON SHOKUBAI CO., LTD.; Kane Ace MX-136 (difunctional, "Kane Ace" is a registered trademark possessed by the manufacturer, omitted below), MX-153 (difunctional), MX-154 (difunctional), MX-217 (trifunctional or higher-functional), MX-227M75 (trifunctional or higher-functional), MX-257 (difunctional), MX-334M75, MX-416 (tetrafunctional), MX-451 (trifunctional), MX-960 (difunctional), and MX-965 (difunctional) manufactured by KANEKA CORPORATION; and ALBIPDX 1000 ("ALBIPDX" is a registered trademark, omitted below), 1005, 1006, 2000, 2002, and 3001, and ALBIDURE EP2240 (difunctional, "ALBIDURE" is a registered trademark, omitted below), and EP5340 (difunctional) manufactured by Evonik Industries AG.

As described above, the elastomer component may be contained in reaction product 12 as a backbone component of the crosslinkable epoxy resin. In this case, the elastomer epoxy resin, which is the crosslinkable epoxy resin containing the elastomer component as a backbone component, has an epoxy group at each end of the elastomer backbone part. Examples of the elastomer epoxy resin include 1,2-polybutadiene-modified bisphenol A glycidyl ether, 1,4-polybutadiene-modified bisphenol A glycidyl ether, polypropylene oxide-modified bisphenol A glycidyl ether, polyethylene oxide-modified bisphenol A glycidyl ether, acrylic rubber-modified bisphenol A glycidyl ether, urethane resin-modified bisphenol A glycidyl ether, polyester resin-modified bisphenol A glycidyl ether, 1,2-polybutadiene-modified glycidyl ether, 1,4-polybutadiene-modified glycidyl ether, polypropylene oxide-modified glycidyl ether, polyethylene oxide-modified glycidyl ether, acrylic rubber-modified glycidyl ether, urethane resin-modified glycidyl ether, polyester resin-modified glycidyl ether, and hydrogenated products thereof.

Examples of commercially available products of the elastomer epoxy resin include EPICLON EXA-4816 ("EPICLON" is a registered trademark possessed by the manufacturer, omitted below), EXA-4822, EXA-4850-150, EXA-4850-1000, TSR-601, and TSR-960 manufactured by DIC Corporation; ADEKA RESIN EBR series ("ADEKA RESIN" is a registered trademark possessed by the manufacturer, omitted below) and EPU series manufactured by ADEKA Corporation; C-1116A/B manufactured by TESK CO., LTD.; Duralco 4583 manufactured by Cotronics Corp.; Albiflex 296, Albiflex 348, Albiflex XP544, and Albiflex 712 manufactured by Evonik Industries AG; EPOFRIEND AT501 and EPOFRIEND CT310 manufactured by Daicel Corporation; D.E.R.732 manufactured by The Dow Chemical Company; and EPB-13 manufactured by Nippon Soda Co., Ltd.

One or more crosslinkable epoxy resins may be used. For adjustment of the epoxy equivalent of the crosslinkable epoxy resin composition and the crosslinking density of reaction product 12, and adjustment of the viscosity of the crosslinkable epoxy resin composition, two or more crosslinkable epoxy resins are preferably used. In the case that the crosslinkable epoxy resin composition contains the trifunctional or higher-functional crosslinkable epoxy resin and difunctional or monofunctional crosslinkable epoxy resin, for example, the content of the trifunctional or higher-functional crosslinkable epoxy resin is preferably 5 to 80%, and more preferably 10 to 60%, as an epoxy equivalent.

The crosslinking agent is crosslinking an epoxy group of the crosslinkable epoxy resin in reaction product 12. The crosslinking agent has a crosslinkable functional group. The crosslinkable functional group is a group capable of reacting with an epoxy group of the crosslinkable epoxy resin. In the case that the crosslinking agent is a mercapto-type crosslinking agent, which has a thiol group, for example, the crosslinkable functional group is a thiol group. "Crosslinking value" of the crosslinking agent refers to the number of epoxy groups reactive with one molecule of the crosslinking agent. In the case that the crosslinking agent is a mercapto-type crosslinking agent, for example, the crosslinking value of the crosslinking agent coincides with the number of thiol groups.

For the crosslinking agent, a known crosslinking agent applicable as a crosslinking agent for crosslinkable epoxy resins can be used. Examples of the type of the crosslinking agent include mercapto-type crosslinking agents, acid anhydride crosslinking agents, and amine crosslinking agents. In order to enhance the processability and adhesion, it is preferred that the type of the crosslinking agent be a mercapto-type crosslinking agent. This is because the sulfur atoms of thiol groups in molecules of the mercapto-type crosslinking agent bond to piezoelectric 10 and electrode pair 30 to enhance the adhesion between reaction product 12 and electrode pair 30 and adhesion between reaction product 12 and piezoelectric 10.

Examples of the crosslinking agent include pentaerythritol tetrakis(3-mercaptobutyrate), 1,3,5-tris(3-mercaptobutyryloxyethyl)-1,3,5-triazine-2,4,6-(1H,3H,5H)trione, trimethylolethane tris(3-mercaptobutyrate) (TEMB), trimethylolpropane tris(3-mercaptobutyrate) (TPMB), trimethylolpropane tris(3-mercaptopropionate) (TMMP), tris-[(3-mercaptopropionyloxy)-ethyl]isocyanurate (TEMPIC), pentaerythritol tetrakis(3-mercaptopropionate) (PEMP), dipentaerythritol hexakis(3-mercaptopropionate) (DPMP), and tetraethylene glycol bis(3-mercaptopropionate) (EGMP-4). Other examples of the crosslinking agent include crosslinking agents described in Japanese Patent Application Laid-Open Nos. 9-40758, 10-77334, and 11-209459.

The crosslinking agent may be synthesized, or a commercially available product may be used for the crosslinking agent. Examples of commercially available products of the crosslinking agent include KarenzMT PE1 (tetravalent, "KarenzMT" is a registered trademark possessed by the manufacturer, omitted below), NR1 (trivalent), TEMB (trivalent), and TPMB (trivalent) manufactured by Showa Denko K.K.; TS-G (tetravalent) manufactured by SHIKOKU CHEMICALS CORPORATION; TMMP (trivalent), TEMPIC (trivalent), PEMP (tetravalent), DPMP (hexavalent), and EGMP-4 (divalent) manufactured by SC Organic Chemical Co., Ltd.; and ST12 (divalent) manufactured by Mitsubishi Chemical Corporation. One or more crosslinking agents may be used.

The crosslinkable epoxy resin composition may further contain an additive, as necessary. Examples of the additive include metal alkoxide compounds.

In order to enhance the processability and adhesion, it is preferred for the crosslinkable epoxy resin composition to further contain the metal alkoxide compound. This is because in the case that the crosslinkable epoxy resin composition further contains the metal alkoxide compound, the residues in molecules of the metal alkoxide compound bond to reaction product 12, piezoelectric 11, and electrode pair 30 to enhance the adhesion between reaction product 12 and piezoelectric 11 and adhesion between reaction product 12 and electrode pair 30.

The type of the metal alkoxide compound can be appropriately selected in any manner such that the advantageous effects of one or more embodiments of the present invention can be achieved. Examples of the metal atom of the metal alkoxide compound include aluminum, zirconium, titanium, silicon, tin, and barium.

Examples of the metal alkoxide compound include monoisocyanatotrialkoxymetal such as 3-isocyanatopropyltriethoxysilane, 3-isocyanatopropyltrimethoxysilane, 2-isocyanatoethyltriethoxysilane, 2-isocyanatoethyltripropoxyzirconium, and 2-isocyanatoethyltributoxytin; monoisocyanatodialkoxymetal such as 3-isocyanatopropylethyldiethoxysilane, 3-isocyanatopropylmethyldiisopropoxytitanium, 2-isocyanatoethylethyldipropoxyzirconium, 2-isocyanatoethylmethyldibutoxytin, and isocyanatomethyldibutoxyaluminum; monoisocyanatomonoalkoxymetal such as 3-isocyanatopropyldiethylethoxysilane, 3-isocyanatopropyldimethylisopropoxytitanium, 2-isocyanatoethyldiethylpropoxyzirconium, 2-isocyanatoethyldimethylbutoxytin, and isocyanatomethylmethylmethoxyaluminum; diisocyanatoalkoxymetal such as di(3-isocyanatopropyl)diethoxysilane and di(3-isocyanatopropyl)methylisopropoxytitanium; and triisocyanatoalkoxymetal such as ethoxysilane triisocyanate.

Other examples of the metal alkoxide compound include metal alkoxide compounds having an epoxy group such as γ-glycidoxypropyltriethoxysilane, γ-glycidoxypropyltrimethoxysilane, γ-glycidoxypropylmethyldimethoxysilane, γ-glycidoxypropyldimethylethoxysilane, γ-glycidoxypropylmethyldiethoxysilane, β-(3,4-epoxycyclohexyl)ethyltrimethoxysilane, 3,4-epoxybutyltrimethoxysilane, γ-glycidoxypropyltriisopropoxytitanium, γ-glycidoxypropylmethyldiisopropoxytitanium, γ-glycidoxypropyldimethylisopropoxytitanium, 3,4-epoxybutyltripropoxyzirconium, 3,4-epoxybutylmethyldipropoxyzirconium, 3,4-epoxybutyldimethylpropoxyzirconium, and β-(3,4-epoxycyclohexyl)ethyltriethoxytin; alkylalkoxysilanes such as methyltrimethylethoxysilane, ethyltriethoxysilane, isopropyltriisopropoxysilane, dimethyldimethoxysilane, diethyldiethoxysilane, diisopropyldiisopropoxysilane, trimethylmethoxysilane, triethylethoxysilane, and triisopropylisopropoxysilane; acid anhydride metal alkoxides such as 3-(triethoxysilyl)-2-methylpropylsuccinic anhydride; acid halide metal alkoxides such as 2-(4-chlorosulfonylphenyl)ethyltriethoxysilane; and alkoxysilanes having an amino group or mercapto group such as 3-aminopropyltrimethoxysilane, 3-aminopropyltriethoxysilane, 3-mercaptopropyltrimethoxysilane, and 3-mercaptopropyltriethoxysilane.

One or more metal alkoxide compounds may be used.

The components contained in reaction product 12 can be confirmed through analysis by using a known instrumental analysis technique such as pyrolysis GC-MS, differential scanning calorimetry (DSC), measurement of degree of swelling, and elemental analysis. For example, the molecular structure of each component contained in reaction product 12 can be estimated through pyrolysis MS. The components contained in reaction product 12 can be estimated from the glass transition temperature, Tg, measured in DSC and the degree of swelling measured in measurement of degree of swelling.

The number of epoxy groups per molecule of the crosslinkable epoxy resin and the crosslinking value of the crosslinking agent can be estimated through comparison between physical properties including Tg and degree of swelling and calibration curves or theoretical values. As the number of epoxy groups per molecule of the crosslinkable epoxy resin and the crosslinking value of the crosslinking agent increase, a higher crosslinking density is imparted to reaction product 12, and hence the degree of swelling tends to be lower and Tg tends to be higher. Accordingly, the number of epoxy groups in the crosslinkable epoxy resin and the crosslinking value of the crosslinking agent can be estimated on the basis of calibration curves representing the relationship between the number of epoxy groups and the crosslinking value and physical properties including degree of swelling and Tg, or on the basis of the theoretical values for the physical properties.

Electrode pair 30 is a pair of electrodes that is disposed with piezoelectric composite 10 sandwiched therebetween and applies a voltage to piezoelectric composite 10. Electrode pair 30 is disposed at least in contact with both end surfaces of piezoelectric 11. In one or more embodiments, electrode pair 30 is disposed in contact with both end surfaces of piezoelectric 11 and both end surfaces of reaction product 12.

The material of electrode pair 30 can be appropriately selected from known materials. Examples of the material of electrode pair 30 include gold, silver, platinum, palladium, nickel, and copper.

[Method for Producing Piezoelectric Element]

Next, the method for producing piezoelectric element 130 will be described. Piezoelectric element 130 can be produced, for example, by using the following first production method or second production method.

(First Production Method)

Figure 2A:
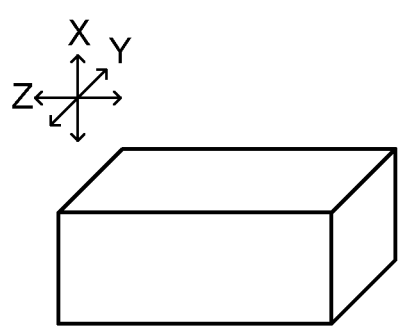
FIGS. 2A to 2E are each a schematic diagram for description of a first production method for a piezoelectric element according to one or more embodiments of the present invention.
Figure 2B:
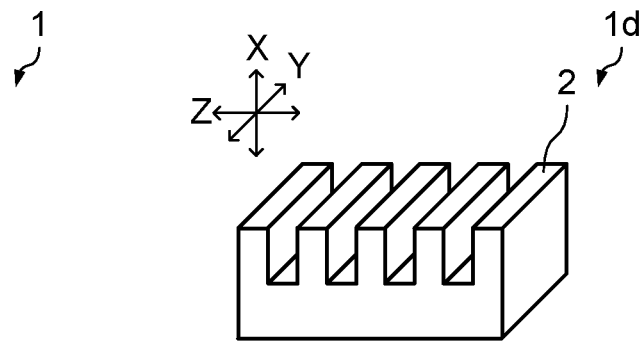
Figure 2C:
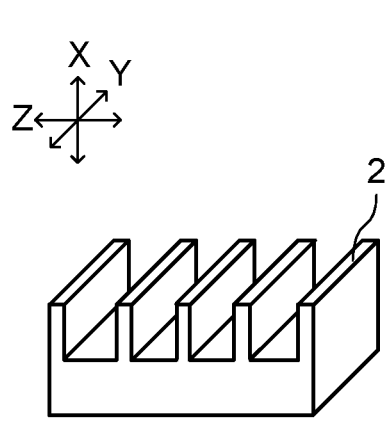
Figure 2D:
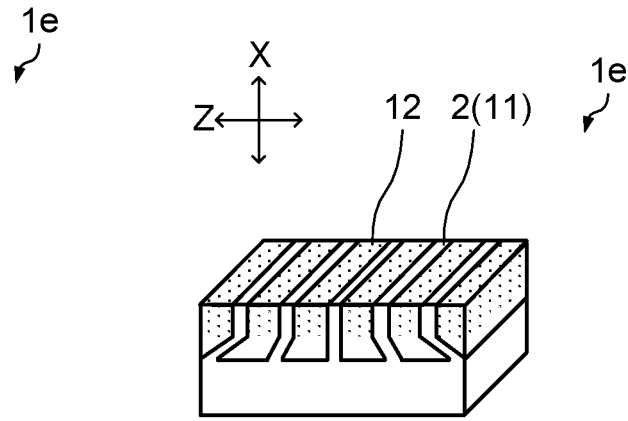
Figure 2E:
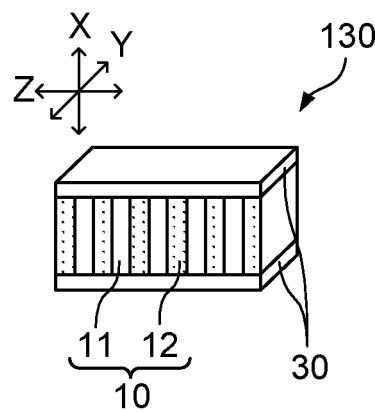

FIGS. 2A to 2E are each a schematic diagram for description of the first production method for piezoelectric element 130. FIG. 2A is a schematic diagram illustrating the shape of a piezoelectric substrate; FIG. 2B is a schematic diagram illustrating the shape of a piezoelectric substrate after dicing (hereinafter, also referred to as "diced substrate 1d", simply); FIG. 2C is a schematic diagram illustrating the shape of diced substrate 1d after etching (hereinafter, also referred to as "etched substrate 1e", simply); FIG. 2D is a schematic diagram illustrating the state in which the crosslinkable epoxy resin composition is filling a plurality of gaps of piezoelectric 11 and cured; and FIG. 2E is a schematic diagram illustrating piezoelectric element 130 produced.

The first production method includes: dicing in which piezoelectric substrate 1 is diced; etching in which diced substrate 1d is etched; filling in which a plurality of gaps of piezoelectric 11 are filled with the crosslinkable epoxy resin composition; crosslinking in which reaction product 12 of the crosslinkable epoxy resin composition is formed; and electrode-forming in which electrode pair 30 is formed.

1) Dicing

First, piezoelectric substrate 1 is prepared (see FIG. 2A). A plurality of grooves are formed in piezoelectric substrate 1 along the Y direction through dicing (see FIG. 2B). Through this dicing, a plurality of plate-like piezoelectric strips 2 are formed. Piezoelectric strips 2 may be completely cut apart. However, it is preferred for easy handling of piezoelectric strips 2 that each of the plurality of piezoelectric strips 2 in alignment be integrally connected to piezoelectric substrate 1. In one or more embodiments, piezoelectric strips 2 are each integrally connected to piezoelectric substrate 1. Such a group of piezoelectric strips 2 is formed through providing piezoelectric substrate 1 with grooves with one end portion in the X direction left ungrooved. Thereby, diced substrate 1d is obtained.

The length (height) of each piezoelectric strip 2 in the X direction is determined by the depth of grooving in dicing. The height of each piezoelectric strip 2 can be appropriately changed so as to form piezoelectric 11 with an intended height. The height of each piezoelectric strip 2 is, for example, 120 to 425 µm.

The length (thickness) of each piezoelectric strip 2 in the Z direction is determined by the interval (pitch) of grooving in dicing. The thickness of each piezoelectric strip 2 can be appropriately changed so as to form piezoelectric 11 with an intended thickness. The thickness of each piezoelectric strip 2 is larger than the thickness of each piezoelectric 11 in piezoelectric element 130 by the depth of a portion to be etched in etching. The thickness of each piezoelectric strip 2 is, for example, 40 to 110 µm.

2) Etching

Subsequently, diced substrate 1d is soaked in an etching solution for etching (see FIG. 2C). Through the etching, the plurality of piezoelectric strips 2 are totally etched in a substantially uniform manner, and piezoelectric strips 2 are shaped to have a constant intended height and thickness. Thereby, etched substrate 1e is obtained. Etching is preferably anisotropic etching.

The etching solution may be prepared, or a commercially available product may be used for the etching solution. The etching solution contains, for example, 0.1 to 20 mass % of ammonium fluoride and 0.1 to 20 mass % of nitric acid. The residual component of the etching solution is typically water. Examples of commercially available products of the etching solution include Pure Etch PT303 manufactured by Hayashi Pure Chemical Ind., Ltd.

Ammonium fluoride dissolves components except lead components and forms insoluble passive substance (lead fluoride). If the ammonium fluoride content of the etching solution is less than 0.1 mass %, insufficient etching may be caused, and if the ammonium fluoride content of the etching solution is more than 20 mass %, homogeneous etching may be inhibited because of excessively quick passivation. From these viewpoints, the ammonium fluoride content of the etching solution is preferably 4 to 10 mass %.

Nitric acid dissolves the passive substance derived from ammonium fluoride and lead components. If the nitric acid content of the etching solution is less than 0.1 mass %, homogeneous removal of the passive substance may be inhibited to lead to insufficient etching, and if the nitric acid content of the etching solution is more than 20 mass %, nitric acid may be decomposed and deactivated when the etching solution is exposed to light. From these viewpoints, the nitric acid content of the etching solution is preferably 0.1 to 10 mass %.

The etching solution may further contain any additional component other than ammonium fluoride and nitric acid in a manner such that the advantageous effects of one or more embodiments of the present invention are successfully exerted. Examples of the additional component include sodium fluoride and hexafluorosilicic acid. One or more additional components may be used. Sodium fluoride promotes etching with the etching solution. The sodium fluoride content of the etching solution is, for example, 0.1 to 19.9 mass %. Hexafluorosilicic acid acts to homogenize the etching rate among the plurality of piezoelectric strips 2. The hexafluorosilicic acid content of the etching solution is, for example, 0.1 to 19.9 mass %.

It is preferred to use a glass container (e.g., a glass Petri dish) in etching. Thereby, passivation due to ammonium fluoride and lead components can be more effectively prevented.

The etching is achieved by sufficiently contacting the surface of piezoelectric strips 2 with the etching solution. For example, the etching is achieved by soaking piezoelectric strips 2 in the etching solution under moderate stirring. "Moderate stirring" refers to stirring at a stirring rate, for example, enough to prevent stagnation of the etching solution in the vicinity of the surface of piezoelectric strips 2 (to continuously feed the etching solution to the surface of piezoelectric strips 2).

An excessively high etching rate in the etching may cause the etching to progress unevenly among a plurality of piezoelectric strips 2. The etching rate is preferably lower than 1 µm/min for achievement of homogenous etching among piezoelectric strips 2. The lower limit of the etching rate can be determined in view of the productivity of piezoelectric element 130, and from this viewpoint the etching rate is preferably 0.04 µm/min or higher.

The etching rate can be adjusted through the contents of the etching components in the etching solution, and, for example, the etching rate can be increased through increasing the contents.

In addition, the etching rate can be adjusted through the temperature of the etching solution, and, for example, the etching rate can be increased through raising the temperature of the etching solution. The temperature of the etching solution is preferably 35° C. or lower for achievement of the above-described etching rate (1 µm/min). The lower limit of the temperature of the etching solution may be any value in the range in which the etching solution can remain as liquid. However, the temperature of the etching solution is preferably normal temperature (e.g., 25° C.) for simplification of temperature control.

Moreover, the etching rate can be adjusted through the presence or absence of stirring of the etching solution or the stirring rate, and, for example, the etching rate can be increased through vigorous stirring of the etching solution. The stirring rate for the etching solution may be any stirring rate enough to prevent stagnation of the etching solution in the vicinity of the surface of piezoelectric strips 2, as described above, and moderate to a degree such that piezoelectric strips 2 are prevented from breaking in etching. In the case of etching with the etching solution placed in a glass Petri dish, for example, stirring can be performed with a magnetic stirrer at a stirring rate of approximately 150 rpm.

The etching is suitable for precise control of the shape, surface roughness, and positioning of each piezoelectric 11.

For example, the etching is suitable for formation of piezoelectric strips 2 each having a width of 30 μm or smaller and a height of 80 μm or larger.

After the etching, washing with hot water, washing with dilute nitric acid, ultrasonic washing, or any combination thereof may be performed, as necessary, for reliable removal of the passive substance. The etching may be repeated a plurality of times so as to obtain piezoelectric 11 having an intended size.

3) Filling

Then, the gaps of the plurality of piezoelectric strips 2 in etched substrate 1e are filled with the crosslinkable epoxy resin composition. Etched substrate 1e can be left to stand with the gaps of the plurality of piezoelectric strips 2 filled with the crosslinkable epoxy resin composition, or the group of piezoelectric strips 2 can be sandwiched in the Z direction at a moderate pressure to adjust the interval between adjacent piezoelectric strips 2 (see FIG. 2D).

In the case that etched substrate 1e is left to stand, the interval can be determined in accordance with the surface tension and viscosity of the crosslinkable epoxy resin composition. For example, the amount of the crosslinkable epoxy resin composition attached to the surface of each piezoelectric strip 2 can be increased (the thickness of the crosslinkable epoxy resin composition attached to the surface can be increased) through increase of the viscosity of the crosslinkable epoxy resin composition. Thus, the interval between piezoelectric strips 2 can be adjusted to a particular interval according to the amount of the crosslinkable epoxy resin composition attached. Accordingly, the interval can be adjusted in accordance with the components contained in the crosslinkable epoxy resin composition.

In the case that the crosslinkable epoxy resin composition contains a resin particle having an adjusted particle size, the crosslinkable epoxy resin composition is disposed with the resin particle sandwiched therebetween adjacent piezoelectric strips 2. As a result, the interval between adjacent piezoelectric strips 2 can be adjusted to a size equal to the particle size of the resin particle.

In the case that the width of each piezoelectric strip 2 is small to a degree such that each piezoelectric strip 2 is distorted by external force, the distance between adjacent piezoelectric strips 2 may be shortened by application of external force with the gaps of piezoelectric strips 2 in etched substrate 1e filled with uncured resin 12.

4) Crosslinking

Subsequently, the epoxy group of the crosslinkable epoxy resin and the crosslinkable functional group of the crosslinking agent are reacted together. Thereby, the epoxy group is crosslinked via the crosslinking agent, and thus reaction product 12 of the crosslinkable epoxy resin composition can be formed. For example, etched substrate 1e filled with the crosslinkable epoxy resin composition is left to stand under an environment at room temperature (e.g., 22 to 26° C.) for 12 hours, and further left to stand under an environment at 50° C. for 3 hours, and thus reaction product 12 can be formed.

5) Electrode-Forming

Finally, a portion not constituting piezoelectric composite 10 including piezoelectric strips 2 (for piezoelectrics 11) and reaction products 12 alternately disposed in alignment is cut out in the X direction, and electrode pair 30 is disposed on the end surfaces of piezoelectric composite 10 in the X direction (see FIG. 2E). The method for forming electrode pair 30 can be appropriately selected from known methods. Examples of the method for forming electrode pair 30 include sputtering, vacuum deposition, and plating. For example, chromium and gold can be suitably formed on each end surface in the order presented through sputtering.

Each of the end surfaces is polished to adjust the surface roughness or adjust the thickness of piezoelectric composite 10 in the X direction before electrode pair 30 is disposed. Polishing can be performed by using a known method such as blasting with an abrasive grain having a particle size of 0.5 μm, 1 μm, or 2 μm. The surface roughness of each end surface is preferably 150 to 250 nm as arithmetic average roughness, Ra, for example, to achieve higher adhesion of electrode pair 30 formed (anchor effect of piezoelectric composite 10).

(Second Production Method)

Figure 3A:
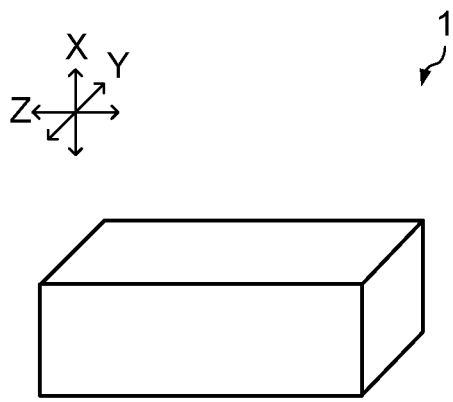
FIGS. 3A to 3F are each a schematic diagram for description of a second production method for a piezoelectric element according to one or more embodiments of the present invention.
Figure 3B:
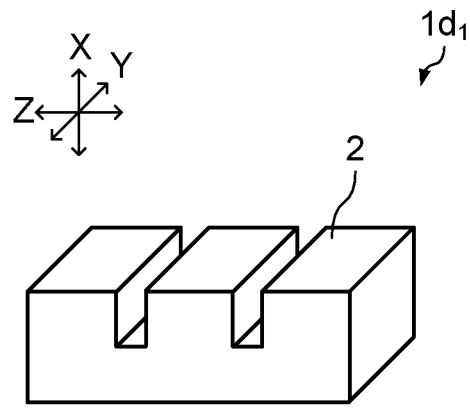
Figure 3C:
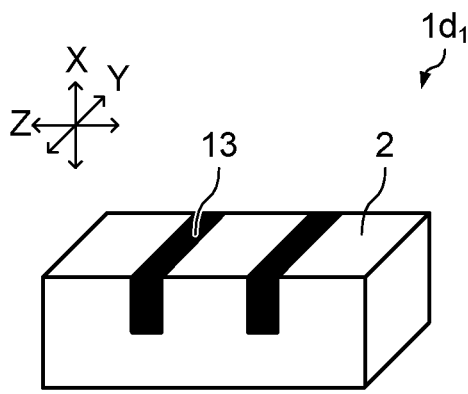
Figure 3D:
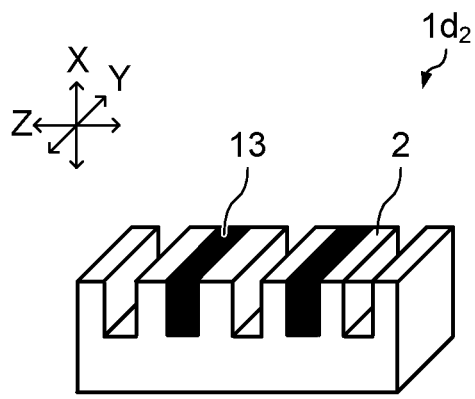
Figure 3E:
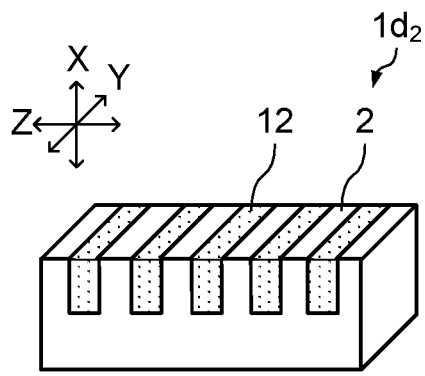
Figure 3F:
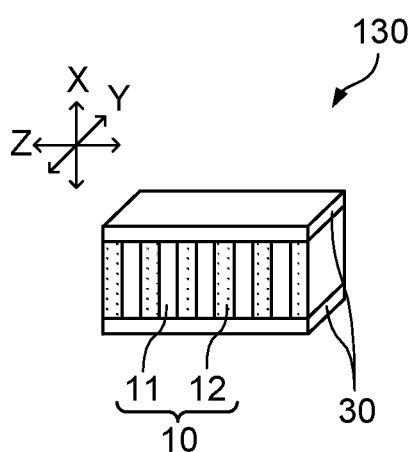

FIGS. 3A to 3F are each a schematic diagram for description of the second production method for piezoelectric element 130. FIG. 3A is a schematic diagram illustrating the shape of a piezoelectric substrate; FIG. 3B is a schematic diagram illustrating the shape of a piezoelectric substrate after first dicing (hereinafter, also referred to as "first diced substrate $1d_1$", simply); FIG. 3C is a schematic diagram illustrating first diced substrate $1d_1$ reinforced with reinforcing agent 13; FIG. 3D is a schematic diagram illustrating the shape of a piezoelectric substrate after second dicing (hereinafter, also referred to as "second diced substrate $1d_2$", simply); FIG. 3E is a schematic diagram illustrating the state in which the crosslinkable epoxy resin composition is filling a plurality of gaps of piezoelectric 11 and cured; and FIG. 3F is a schematic diagram illustrating piezoelectric element 130 produced.

The second production method includes: first dicing in which piezoelectric substrate 1 is diced; reinforcing in which the grooves of first diced substrate $1d_1$ are filled with reinforcing agent 13; second dicing in which diced substrate $1d_1$ filled with reinforcing agent 13 is further diced; filling in which the gaps of a plurality of piezoelectric strips 2 (for piezoelectrics 11) in second diced substrate $1d_2$ are filled with the crosslinkable epoxy resin composition; crosslinking in which reaction product 12 of the crosslinkable epoxy resin composition is formed; and electrode-forming in which electrode pair 30 is formed.

1) First Dicing

First, piezoelectric substrate 1 is prepared (see FIG. 3A). Grooves are formed in piezoelectric substrate 1 through dicing in the same manner as the dicing in the first production method to obtain first diced substrate $1d_1$ (see FIG. 3B). The thickness of each piezoelectric strip 2 formed in the first dicing can be appropriately changed to form piezoelectric 11 with an intended thickness.

2) Reinforcing

Subsequently, the grooves of first diced substrate $1d_1$ are filled with reinforcing agent 13 and reinforcing agent 13 is cured (see FIG. 3C). Thereby, first diced substrate $1d_1$ is reinforced, and simultaneously the outer shape of first diced substrate $1d_1$ can be returned to that before being diced. Examples of reinforcing agent 13 include photoresists, ultraviolet-curable resins, thermosetting resins, two-component curable resins, and waxes.

3) Second Dicing

Then, grooves are further formed in first diced substrate $1d_1$ through dicing with the previously-formed grooves filled with reinforcing agent 13 cured to obtain second diced substrate $1d_2$ (see FIG. 3D). More specifically, grooves parallel to the grooves formed in the first dicing are formed at constant intervals. Thereby, a plurality of piezoelectric strips 2 each having an intended thickness are formed.

4) Filling

Subsequently, reinforcing agent 13 in the grooves of second diced substrate $1d_2$ is removed. Reinforcing agent 13 is removed, for example, by using an organic solvent capable of dissolving reinforcing agent 13 therein. Reinforcing agent 13 can be removed through soaking of second diced substrate $1d_2$ in the organic solvent. Then, the gaps of the plurality of piezoelectric strips 2 in second diced substrate $1d_2$ are filled with the crosslinkable epoxy resin composition, in the same manner as the filling in the first production method.

5) Crosslinking

Reaction product 12 of the crosslinkable epoxy resin composition is formed in the same manner as the crosslinking in the first production method (see FIG. 3E).

6) Electrode-Forming

Finally, in the same manner as the electrode-forming in the first production method, a portion not constituting piezoelectric composite 10 including piezoelectric strips 2 (for piezoelectrics 11) and reaction products 12 alternately disposed in alignment is cut out in the X direction, the end surfaces of piezoelectric composite 10 in the X direction are polished, and electrode pair 30 is then disposed on the end surfaces of piezoelectric composite 10 (see FIG. 3F).

Piezoelectric element 130 can be produced by using any of the above procedures. Although a case that piezoelectric element 130 is produced from one piezoelectric substrate 1 is described in the description of the first production method and the second production method, the method for producing piezoelectric element 130 is not limited to the above modes. As described in Japanese Patent Application Laid-Open No. 6-224487, for example, it is possible that two piezoelectric substrates in each of which a plurality of piezoelectric strips are formed are superimposed so that the piezoelectric strips are engaged together in a staggered manner and the gaps among the piezoelectric strips are filled with the crosslinkable epoxy resin composition.

The plurality of piezoelectrics 11 in piezoelectric element 130 according to one or more embodiments are disposed in alignment at intervals of 1 to 10 µm. Piezoelectric element 130 has high sensitivity to ultrasound because of the small intervals of the plurality of piezoelectrics 11. The ratio of the length in the facing direction to the length in the alignment direction (aspect ratio) in each piezoelectric 11 is 5 or higher. This ratio permits generation of vibrations primarily in the facing direction. As a result, a sufficient electromechanical coupling factor is achieved.

Further, the stress transmitted to reaction product 12 can be concentrated to piezoelectrics 11 in the case that reaction product 12 is more flexible than electrode pair 30, and hence the sensitivity of piezoelectric element 130 can be enhanced by allowing the stress to concentrate to piezoelectrics 11. Also from these viewpoints, it is preferred for reaction product 12 to contain a flexible elastomer component.

If the aspect ratio is high and the intervals of the plurality of piezoelectrics are small, on the other hand, interaction takes place between adjacent piezoelectrics to lower the electromechanical coupling factor in many cases. However, reaction product 12 in piezoelectric element 130 according to one or more embodiments is formed of a cured product of a crosslinkable epoxy resin composition containing an elastomer component, a crosslinkable epoxy resin, and a crosslinking agent, and one or each of the number of epoxy groups possessed by the crosslinkable epoxy resin per molecule and the crosslinking value of the crosslinking agent is 3 or more. The flexible elastomer component contained in reaction product 12 can prevent lowering of the electromechanical coupling factor due to interaction between adjacent piezoelectrics 11.

If a flexible elastomer component is contained in the reaction product, on the other hand, the adhesion between the reaction product and the piezoelectric is typically lowered, and the reaction product may be peeled off from the piezoelectric in polishing each end surfaces of the piezoelectric composite. In other words, insufficient processability may be imparted to the piezoelectric composite. In the case that an electrode pair is formed on the end surfaces of the piezoelectric and the end surfaces of the reaction product, the adhesion between the reaction product and the electrode pair may be lowered and cause peeling-off of the electrode pair from the piezoelectric composite, even if the processability is sufficient. However, reaction product 12 in piezoelectric element 130 according to one or more embodiments is formed of a cured product of a crosslinkable epoxy resin composition containing one or both of a trifunctional or higher-functional crosslinkable epoxy resin and a trivalent or higher-valent crosslinking agent. This configuration can enhance the adhesion between reaction product 12 and piezoelectric 11, even though reaction product 12 contains the flexible elastomer component. As a result, enhanced processability is imparted to piezoelectric composite 10.

If a flexible elastomer component is contained in the reaction product, the adhesion between the reaction product and an electrode is typically lowered as well. As a result, the electrode may be peeled off from the piezoelectric composite. However, the adhesion between reaction product 12 and electrode pair 30 can be enhanced in piezoelectric element 130 according to one or more embodiments, and hence electrode pair 30 is prevented from being peeled off from piezoelectric composite 10.

Modification

Figure 4A:
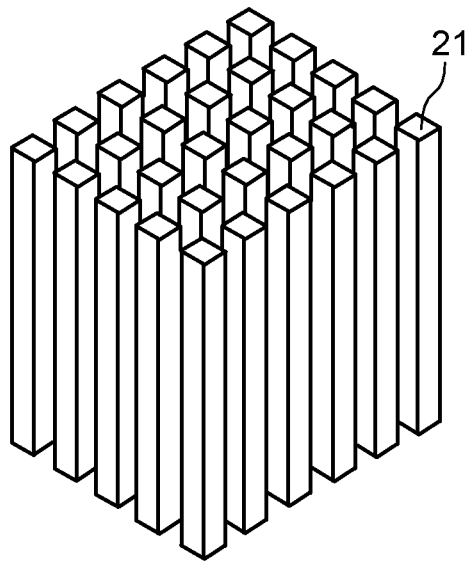
FIGS. 4A and 4B each illustrate the shape of a piezoelectric according to a modification of one or more embodiments of the present invention.
Figure 4B:
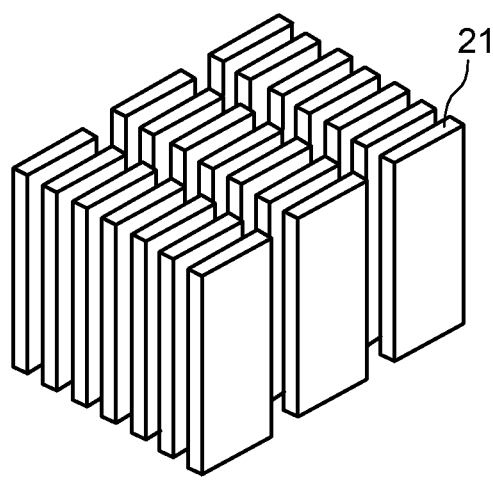

FIGS. 4A and 4B each illustrate the shape of piezoelectric 21 according to a modification of one or more embodiments of the present invention. Although the case that the shape of each piezoelectric 11 is a plate is described for the above embodiments, the shape of the piezoelectric according to the present invention is not limited to a plate. The shape of the piezoelectric may be, for example, a column, as illustrated in FIGS. 4A and 4B. In this case, the alignment direction of a plurality of piezoelectrics 21 coincides with the Y direction and Z direction, and the plurality of piezoelectrics 21 are disposed in alignment at intervals in the plane direction (YZ direction). The height direction of piezoelectric 21 (X direction) is a direction intersecting a plane lying along the alignment direction of piezoelectrics 21 (YZ plane).

The shape of the cross-section of the "column" is typically rectangular, and may be a square as illustrated in FIG. 4A, or may be a rectangle as illustrated in FIG. 4B. The height-width ratio of the shape of the cross-section is preferably 1:1 to 1:5, and more preferably 1:1 to 1:1.5. It is more preferred that the shape of the cross-section of each piezoelectric 21 be a circle.

The piezoelectric element including columnar piezoelectrics 21 can be produced, for example, by using the first production method, which includes etching, or the second production method, which includes a plurality of dicings.

In the case that the piezoelectric element including columnar piezoelectrics 21 is produced by using the first production method, dicing is performed in the dicing to form a plurality of grooves along the Y direction and a plurality of grooves along the Z direction. Thereby, a plurality of columnar piezoelectric strips 2 each having an intended size can be formed in the Y direction and Z direction.

In the case that the piezoelectric element including columnar piezoelectrics 21 is produced by using the second production method, second reinforcing in which the grooves of second diced substrate $1d_2$ are filled with reinforcing agent 13 and reinforcing agent 13 is cured, and third dicing in which, in addition to the previously-formed grooves of second diced substrate $1d_2$, grooves are further formed in a direction perpendicular to the previously-formed grooves of second diced substrate $1d_2$ (Z direction) in the plane direction (YZ direction), with the previously-formed grooves filled with reinforcing agent 13 cured, are further performed between the second dicing and the filling. Thereby, a plurality of columnar piezoelectric strips 2 each having a constant intended width are formed in the Y direction and Z direction.

Figure 5:
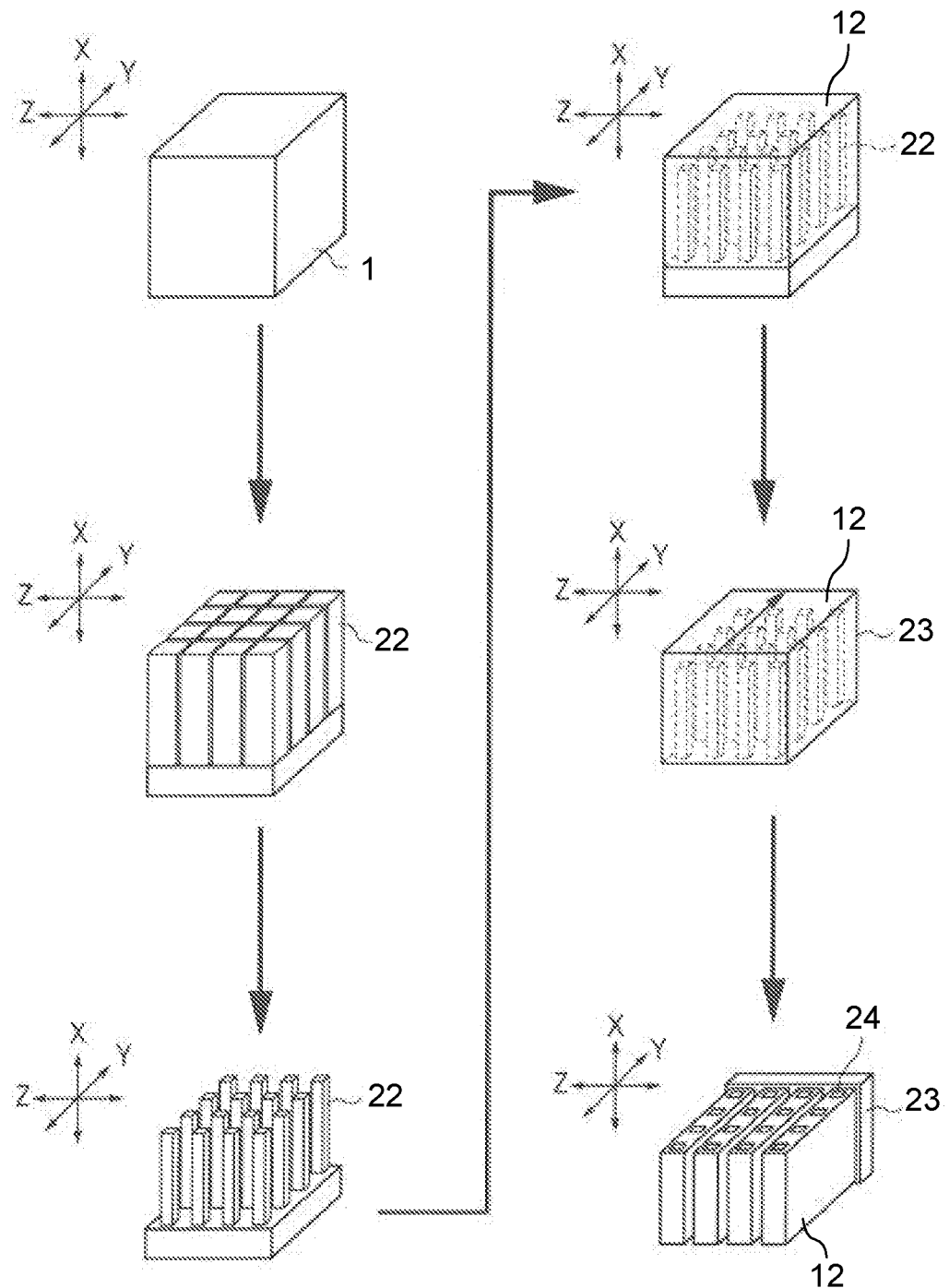
FIG. 5 schematically illustrates the first half of one example of a process for producing a piezoelectric element including columnar piezoelectrics from a piezoelectric substrate.
Figure 6:
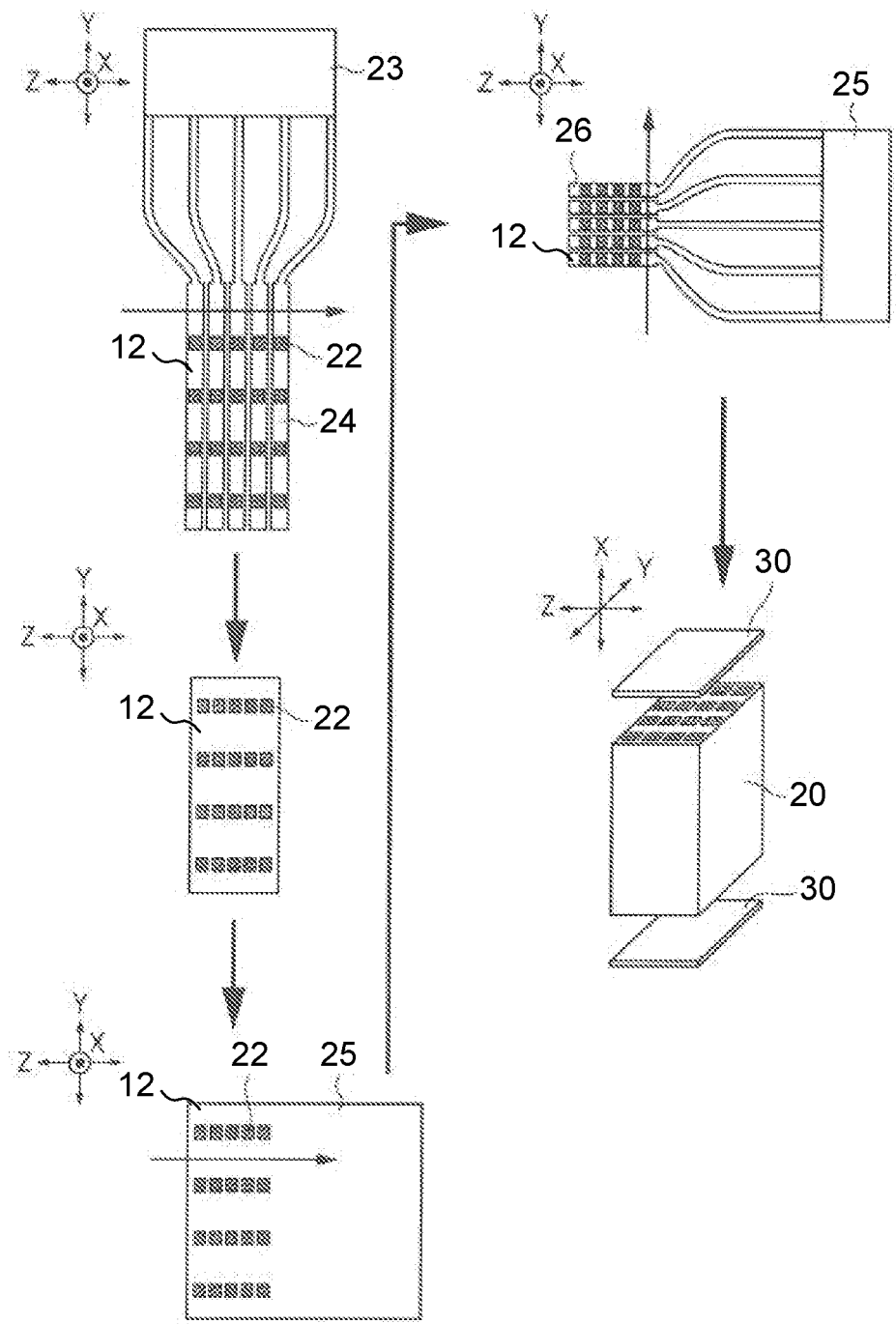
FIG. 6 schematically illustrates the latter half of one example of a process for producing a piezoelectric element including columnar piezoelectrics from a piezoelectric substrate.

Alternatively, the piezoelectric element including columnar piezoelectrics 21 can be produced by using the following production method. FIG. 5 schematically illustrates the first half of the process for producing the piezoelectric element including columnar piezoelectrics 21, and FIG. 6 schematically illustrates the latter half of the process for producing the piezoelectric element including columnar piezoelectrics 21.

In the case that the piezoelectric element including columnar piezoelectrics 21 is produced, grooves are formed in piezoelectric substrate 1 in the Y direction and Z direction in dicing. Thereby, columnar piezoelectric strips 22 are formed, where the width direction is the Y direction and Z direction and the height direction is the X direction. The grooves are formed with one end portion in the X direction left ungrooved, and one end of each of the plurality of piezoelectric strips 22 in alignment is integrally connected to the end portion of piezoelectric substrate 1. The depth of grooving (the length of each piezoelectric strip 22 in the X direction) is, for example, 120 to 425 µm.

Also in the case that the piezoelectric element including columnar piezoelectrics 21 is produced, piezoelectric strips 22 are etched with the above-described etching solution as with the case of the first production method. Thereby, the plurality of piezoelectric strips 22 in alignment are totally etched in a substantially uniform manner, and shaped to have a substantially constant, intended width.

Subsequently, the gaps of adjacent piezoelectric strips 22 etched are filled with the crosslinkable epoxy resin composition (first filling). Next, reaction product 12 of the crosslinkable epoxy resin composition is formed (first crosslinking). Thus, piezoelectric strips 22 are included in reaction product 12 with the positional relationship in the YZ direction after etching substantially maintained. A part of reaction product 12 including piezoelectric strips 22 is cut out from one end portion of piezoelectric substrate 1, and used as primary inclusion body 23.

Then, the resin portion of primary inclusion body 23 is cut along the X direction to produce first resin plate portions 24 (first arranging). Each first resin plate portion 24 is formed through cutting the resin portion with one end portion in the Y direction left uncut, and is a plate-shaped mass of resin including the plurality of piezoelectric strips 22 disposed in a line along the Z direction.

Subsequently, the plurality of first resin plate portions 24 in alignment in primary inclusion body 23 are soaked in a slurry containing the above-described spherical resin particle, and then dried. Thus, the resin particle is introduced between adjacent first resin plate portions 24, and the intervals of first resin plate portions 24 are adjusted to a constant value (first gap-adjusting).

Then, the gaps of the plurality of first resin plate portions 24 with the intervals adjusted are further filled with the crosslinkable epoxy resin composition (second filling). Next, reaction product 12 of the crosslinkable epoxy resin composition is formed (second crosslinking). Thereby, secondary inclusion body 25 including piezoelectric strips 22 fixed at intended intervals in the Z direction is produced. Secondary inclusion body 25 has a portion of reaction product 12 at one end in the Z direction to facilitate subsequent gap adjustment operation in the Y direction.

Subsequently, the resin portions between piezoelectric strips 22 in secondary inclusion body 25 are cut along the Z direction to produce second resin plate portions 26 (second arranging). Each second resin plate portion 26 is formed through cutting the portion of reaction product 12 with one end portion in the Z direction left uncut, and is a plate-shaped mass of resin including the plurality of piezoelectric strips 22 disposed in a line along the Z direction.

Subsequently, second resin plate portions 26 in secondary inclusion body 25 are soaked in the above slurry, and then dried. Thus, the above resin particle is introduced between adjacent second resin plate portions 26, and the intervals of second resin plate portions 26 are adjusted to a constant value (second gap-adjusting).

Then, the gaps of the plurality of second resin plate portions 26 with the intervals adjusted in secondary inclusion body 25 are filled with the above crosslinkable epoxy resin composition (third filling). Next, reaction product 12 of the crosslinkable epoxy resin composition is formed (third crosslinking). Thereby, piezoelectric strips 22 are fixed not only in the Z direction but also in the Y direction at intended intervals. The group of second resin plate portions 26 with the intervals in the Y direction adjusted is cut out of secondary inclusion body 25, and thus a final inclusion body is obtained.

The final inclusion body is directly used or cut into a piece with an intended length (e.g., 100 to 300 µm) in the X direction, and thus piezoelectric composite 20 including piezoelectrics 21 and reaction products 12 alternately disposed in alignment is obtained. Each of the end surfaces of piezoelectric composite 20 in the X direction is polished, as necessary, to adjust the surface roughness, and electrode pair 30 is formed on the end surfaces. Thus, a piezoelectric element including piezoelectric composite 20 including columnar piezoelectrics 21 and reaction products 12 alternately disposed in both of the Y direction and Z direction is produced.

This production method includes first arranging in which a portion of reaction product 12 is diced to produce first resin plate portions 24, and second arranging in which a portion of reaction product 12 is diced to produce second resin plate portions 26. Since the adhesion between reaction product 12 and piezoelectric 21 (piezoelectric strip 22) is high and the piezoelectric composite has sufficient processability as described above, reaction product 12 can be prevented from being peeled off from piezoelectric 21 (piezoelectric strip 22) in dicing a portion of reaction product 12.

Piezoelectric element 130 is applicable to an ultrasound probe. The ultrasound probe can include, for example, an ultrasound transducer including a plurality of piezoelectric elements 130 disposed in alignment. Since piezoelectric element 130 has excellent piezoelectric properties, an ultrasound probe including piezoelectric element 130 has excellent transmission/reception sensitivity, and can achieve both high spatial resolution and long-distance measurement.

[Configuration of Ultrasound Probe]

Figure 7:
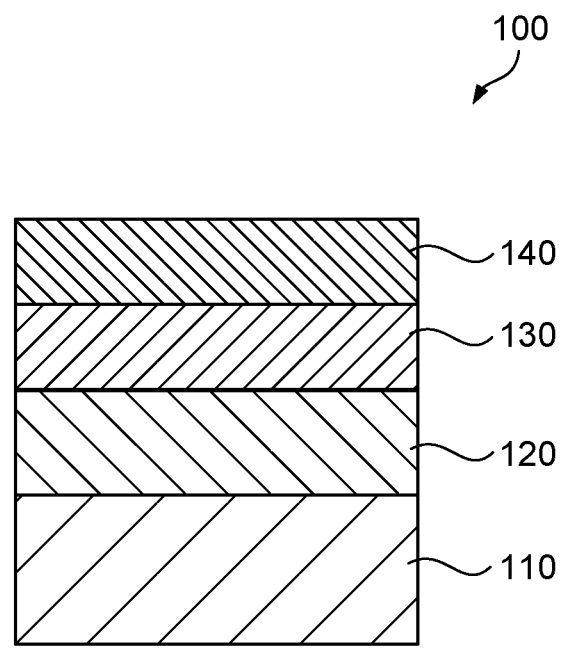
FIG. 7 is a schematic cross-sectional view illustrating one example of the configuration of an ultrasound probe according to one or more embodiments of the present invention.

FIG. 7 is a schematic cross-sectional view illustrating the configuration of ultrasound probe 100 according to one or more embodiments. Ultrasound probe 100 according to one or more embodiments includes back layer 110, acoustic reflection layer 120, piezoelectric element 130, acoustic matching layer 140, and a flexible printed circuit board (FPC) not illustrated.

Back layer 110 is an ultrasound absorber that has an acoustic impedance higher than that of piezoelectric element 130 and absorbs unnecessary ultrasound. In one or more embodiments, back layer 110 is supporting acoustic reflection layer 120. Back layer 110 is provided to the surface opposite to the direction of transmission/reception of ultrasound to/from a subject (e.g., a living body), i.e., the back, of piezoelectric element 130, and absorbs ultrasound generated in the side opposite to the direction of a subject.

Examples of the material of back layer 110 include natural rubber, ferrite rubber, epoxy resin, silicone resin, thermoplastic resin, and resin-based composite materials obtained by subjecting a mixture of at least one of these materials and a powder of tungsten oxide, titanium oxide, ferrite, or the like to press molding. Other examples of the material of back layer 110 include materials obtained by mixing any of the resin-based composite materials crushed and another material such as thermoplastic resin and epoxy resin followed by curing.

Examples of the thermoplastic resin include vinyl chloride, polyvinyl butyral, ABS resin, polyurethane, polyvinyl alcohol, polyethylene, polypropylene, polyacetal, polyethylene terephthalate, fluororesin, polyethylene glycol, and polyethylene terephthalate-polyethylene glycol copolymer. Especially, the resin-based composite materials are preferred, and among them rubber-based composite materials and epoxy resin-based composite materials are particularly preferred for the material of back layer 110.

A compounding agent may be added to back layer 110, as necessary. For example, an inorganic material such as Macor glass and glass or a porous material having voids may be added to back layer 110 to adjust the acoustic impedance of back layer 110.

The shape of back layer 110 can be appropriately determined in accordance with the shape of piezoelectric element 130 or ultrasound probe 100 including piezoelectric element 130.

The thickness of back layer 110 is preferably 1 to 10 mm, and more preferably 1 to 5 mm.

Back layer 110 and the FPC described later can be bonded to each other, for example, with an adhesive commonly used in the art (e.g., an epoxy adhesive).

Acoustic reflection layer 120 has an acoustic impedance higher than that of piezoelectric element 130. Acoustic reflection layer 120 is provided to the surface opposite to the direction of transmission/reception of ultrasound to/from a subject, i.e., the back, of piezoelectric element 130, and reflects ultrasound transmitted to the side opposite to the direction of a subject. In order to enhance the sensitivity to ultrasound, it is preferred for ultrasound probe 100 to include acoustic reflection layer 120.

Examples of the material of acoustic reflection layer 120 include tungsten and tantalum. Especially, it is preferred that the material of acoustic reflection layer 120 be tungsten carbide. An additional compounding agent may be added to acoustic reflection layer 120, as necessary.

The thickness of acoustic reflection layer 120 is preferably 50 μm to 1 mm, and more preferably 150 μm to 250 μm.

Piezoelectric element 130 is capable of converting an electric signal to mechanical vibration, and further capable of converting mechanical vibration to an electric signal. In order to enhance the adhesion between piezoelectric element 130 and acoustic reflection layer 120, it is preferred that piezoelectric element 130 and acoustic reflection layer 120 be at least partially bonded to each other via an adhesive layer. For example, a silicone adhesive or an epoxy adhesive can be used for the material of the adhesive layer. Piezoelectric element 130 is the above-described piezoelectric element.

Acoustic matching layer 140 is a layer that the acoustic impedance of piezoelectric element 130 and that of a subject are matched to prevent the reflection of ultrasound at the interface. For this purpose, acoustic matching layer 140 has a generally intermediate acoustic impedance between those of piezoelectric element 130 and a subject. Acoustic matching layer 140 is disposed in the subject side (surface side) of piezoelectric element 130, for example, via the other electrode described above.

Acoustic matching layer 140 may be a monolayer or laminate. In order to adjust the acoustic properties, however, acoustic matching layer 140 is preferably a laminate of a plurality of layers having different acoustic impedances, for example, two or more layers, more preferably four or more layers. The thickness of acoustic matching layer 140 is preferably $\lambda/4$, where $\lambda$ denotes the wavelength of ultrasound.

For example, acoustic matching layer 140 can be composed of various materials. The acoustic impedance of acoustic matching layer 140 is preferably set so as to approach stepwise or continuously to the acoustic impedance of a subject toward an acoustic lens, and can be adjusted, for example, through the type or content of an additive to be added to the material.

Examples of the material of acoustic matching layer 140 include aluminum, aluminum alloy (e.g., Al—Mg alloy), magnesium alloy, Macor glass, glass, fused quartz, copper graphite, and resin. Examples of the resin include polyethylene, polypropylene, polycarbonate, ABS resin, AAS resin, AES resin, nylons such as nylon 6 and nylon 66, polyphenylene oxide, polyphenylene sulfide, polyphenylene ether, polyether ether ketone, polyamideimide, polyethylene terephthalate, epoxy resin, and urethane resin.

Examples of the additive include zinc oxide, titanium oxide, silica, alumina, red iron oxide, ferrite, tungsten oxide, ytterbium oxide, barium sulfate, tungsten, molybdenum, glass fibers, and silicone particles.

The FPC includes wiring which corresponds to piezoelectric element 130 and is, for example, connected to electrode pair 30 that applies a voltage to piezoelectric 11. For example, the FPC includes wiring for signal-leading to be connected to one electrode of electrode pair 30 and wiring for ground-leading to be connected to the other electrode of electrode pair 30, though the configuration is not illustrated. The FPC may be any commercially available product having the suitable pattern.

Ultrasound probe 100 includes piezoelectric element 130. Accordingly, ultrasound probe 100 can achieve high sensitivity to ultrasound.

If a flexible elastomer component is contained in reaction product 12, the epoxy resin typically swells by the influence of an agent such as an antiseptic solution and fatty acid contained in the human skin. As a result, the sensitivity of the ultrasound probe may decrease over time. However, reaction product 12 in piezoelectric element 130 according to one or more embodiments is formed of a cured product of a crosslinkable epoxy resin composition containing one or both of a trifunctional or higher-functional crosslinkable epoxy resin and a trivalent or higher-valent crosslinking agent. This configuration imparts higher hardness to reaction product 12, and the swelling of the epoxy resin can be prevented. As a result, ultrasound probe 100 can achieve excellent durability.

Ultrasound probe 100 is suitably used for an ultrasound imaging apparatus. The ultrasound imaging apparatus can be configured in the same manner as known ultrasound imaging apparatuses except piezoelectric element 130 in ultrasound probe 100. For example, the ultrasound imaging apparatus is suitable for an ultrasound diagnostic apparatus for medical use and a non-destructive ultrasound inspection apparatus.

[Configuration of Ultrasound Imaging Apparatus]

Figure 8A:
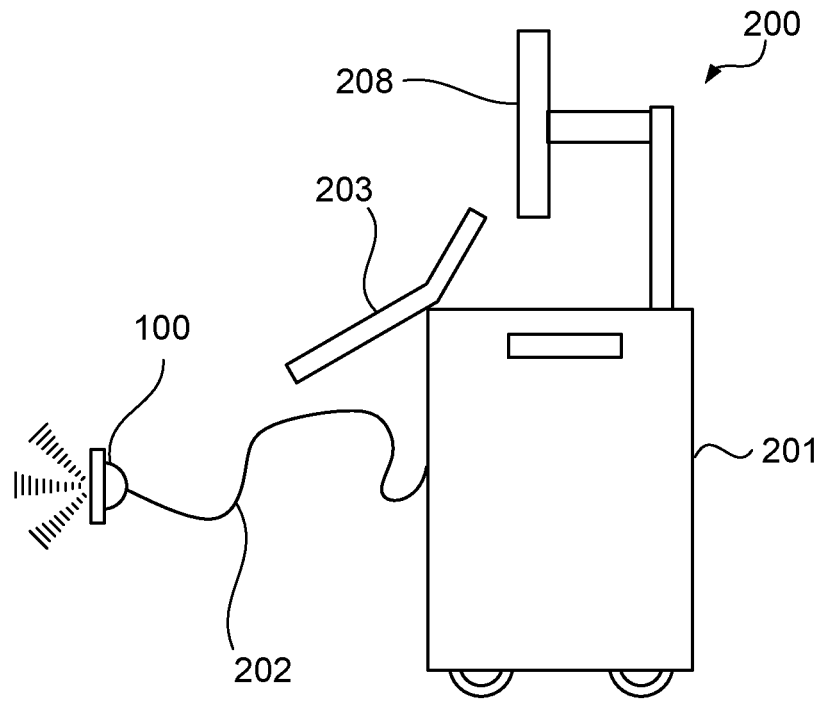
FIGS. 8A and 8B are respectively a diagram schematically illustrating one example of the configuration of an ultrasound imaging apparatus according to one or more embodiments of the present invention and a block diagram illustrating one example of the electric configuration of the ultrasound imaging apparatus.
Figure 8B:
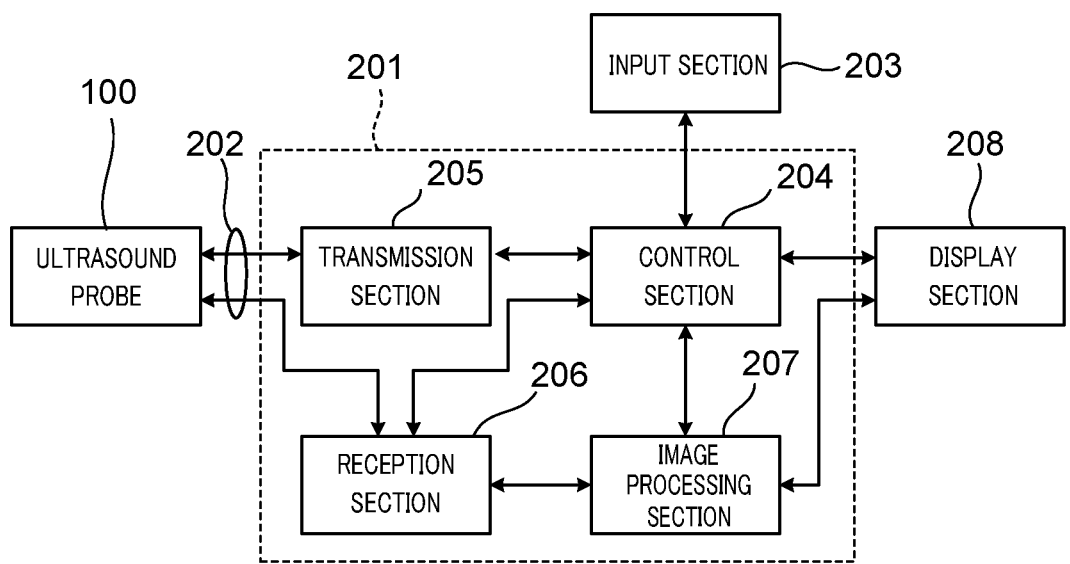

FIGS. 8A and 8B are respectively a diagram schematically illustrating the configuration of ultrasound imaging apparatus 200 according to one or more embodiments and a block diagram illustrating the electric configuration of ultrasound imaging apparatus 200.

As illustrated in FIG. 8A, ultrasound imaging apparatus 200 includes apparatus main body 201; ultrasound probe 100 connected to apparatus main body 201 via cable 202; and input section 203 and display section 208 disposed above apparatus main body 201.

As illustrated in FIG. 8B, apparatus main body 201 includes control section 204 connected to input section 203; transmission section 205 and reception section 206 each connected to control section 204 and cable 202; and image processing section 207 connected to reception section 206 and control section 204. Control section 204 and image processing section 207 are each connected to display section 208.

Cable 202 connects ultrasound probe 100 with transmission section 205, and connects ultrasound probe 100 with reception section 206, and transfers signals.

Input section 203 is a device that inputs commands to initiate diagnosis and so on and data such as personal information on a subject, and is, for example, an operation panel including a plurality of input switches or a keyboard.

Control section 204 has a configuration including, for example, a microprocessor, a storage element, and a peripheral circuit for them. Control section 204 is a circuit that controls the whole of ultrasound imaging apparatus 200 through controlling ultrasound probe 100, input section 203, transmission section 205, reception section 206, image processing section 207, and display section 208 in accordance with their functions.

Transmission section 205 transmits a signal, for example, from control section 204 to ultrasound probe 100 via cable 202.

Reception section 206 receives a signal, for example, from ultrasound probe 100 via cable 202, and output the signal to control section 204 or image processing section 207.

Image processing section 207 is a circuit that forms an image (ultrasonic image) representing the internal state of a subject, for example, on the basis of the signal received in reception section 206 under control by control section 204. Image processing section 207 includes, for example, a digital signal processor (DSP) that forms an ultrasonic image of a subject; a digital-to-analog conversion circuit (DAC circuit) that converts a digital signal processed by the DSP to an analog signal; and so on.

Display section 208 is a device that displays an ultrasonic image of a subject, for example, formed in image processing section 207 under control by control section 204. Display section 208 is, for example, a display device such as a CRT display, a liquid crystal display (LCD), an organic EL display, and a plasma display, or a printing device such as a printer.

In ultrasound imaging apparatus 200, control section 204 receives a signal from input section 203 and outputs a signal toward transmission section 205 to control transmission section 205 to transmit ultrasound (first ultrasonic signal) to a subject such as a living body, and controls reception section 206 to receive an electric signal corresponding to the ultrasound from the inside of the subject (second ultrasonic signal) as response to the first ultrasonic signal.

The electric signal received in reception section 206 is sent to image processing section 207, and processed into an image signal corresponding to the electric signal. The image signal is sent to display section 208, and an image corresponding to the image signal is displayed on display section 208. Information input in input section 203 is sent to display section 208 via control section 204, and display section 208 additionally displays an image and operation (e.g., display of characters, move and magnification of the displayed image) according to the information.

Ultrasound imaging apparatus 200 includes ultrasound probe 100. Accordingly, ultrasound imaging apparatus 200 can provide an ultrasonic image of a subject with high spatial resolution.

[Exemplary Configurations of Present Invention]

As is clear from the above description, the piezoelectric element according to one or more embodiments of the present invention includes a piezoelectric composite and an electrode pair that is disposed to face each other with the piezoelectric composite sandwiched therebetween and applies a voltage to the piezoelectric composite. The piezoelectric composite includes a plurality of piezoelectrics disposed in alignment along a direction perpendicular to the facing direction of the electrode pair at an interval of 1 to 10 µm, wherein the ratio of the length in the facing direction to the length in the alignment direction in each piezoelectric is 5 or higher; and a reaction product of a crosslinkable epoxy resin composition containing an elastomer component, a crosslinkable epoxy resin, and a crosslinking agent, the reaction product filling a gap of the plurality of piezoelectrics, wherein one or each of the number of epoxy groups possessed by the crosslinkable epoxy resin per molecule and the crosslinking value of the crosslinking agent is 3 or more.

By virtue of this configuration, interaction which takes place between adjacent piezoelectrics is prevented in the piezoelectric element, even in the case that the aspect ratio of each piezoelectric is high and the gaps of the plurality of piezoelectrics are small. In addition, the piezoelectric element is excellent with regard to the processability of the piezoelectric composite, the adhesion between the piezoelectric and the reaction product, and chemical durability.

The configuration in which the electrode pair is disposed on both end surfaces of each of the piezoelectrics and both end surfaces of the reaction product is effective for the productivity of the piezoelectric element. Since the piezoelectric element is excellent with regard to the adhesion between the reaction product and the electrodes, the electrode pair can be prevented from peeling off from the piezoelectric composite.

The configuration in which the elastomer component is an elastomer particle having a number average primary particle size of 1 µm or smaller is even more effective for the processability and the adhesion between the piezoelectric composite and the electrode pair.

The configuration in which the elastomer component is silicone elastomer is even more effective for achievement of a sufficient electromechanical coupling factor.

The configuration in which the crosslinkable epoxy resin contains a trifunctional or higher-functional crosslinkable epoxy resin and the trifunctional or higher-functional crosslinkable epoxy resin includes a constitutional unit having an epoxy group is even more effective for increase of the crosslinking density of the reaction product to achieve a sufficient electromechanical coupling factor.

The configuration in which the crosslinkable epoxy resin contains a trifunctional or higher-functional crosslinkable epoxy resin and the trifunctional or higher-functional crosslinkable epoxy resin includes no constitutional unit is even more effective for increase of the crosslinking density of the reaction product to enhance the processability, adhesion, and durability.

The configuration in which the crosslinkable epoxy resin has an aromatic ring in the molecular structure is even more effective for increase of the crosslinking density of the reaction product to enhance the processability, adhesion, and durability, because of the interaction between the aromatic rings.

The configuration in which the crosslinking agent has a thiol group and the reaction product and each piezoelectric are bonded together via the sulfur atom of the thiol group is even more effective for enhancement of the processability and adhesion.

The configuration in which the crosslinkable epoxy resin composition further contains a metal alkoxide compound, and the reaction product and each piezoelectric are bonded together via the residue of the metal alkoxide compound is even more effective for enhancement of the processability and adhesion.

An ultrasound probe including the piezoelectric element can achieve high sensitivity to ultrasound.

The ultrasound imaging apparatus according to one or more embodiments includes the ultrasound probe. Accordingly, the ultrasound imaging apparatus can provide an ultrasonic image of a subject with high spatial resolution.

Examples

Hereinafter, embodiments of the present invention will be described in more detail with reference to Examples.

[Production of Piezoelectric Element 1]

A PMN-PT substrate (manufactured by JFE MINERAL COMPANY, LTD.) with a size of 20 mm×20 mm and a thickness of 5 mm was prepared. The PMN-PT substrate was then diced. Specifically, a plurality of grooves penetrating the PMN-PT substrate in the longitudinal direction (Y direction) and the thickness direction (Z direction) and Opening to the height direction (X direction) was formed by using an automatic dicing saw (DAD3350: manufactured by DISCO Corporation). Thus, a diced substrate including a group of columnar piezoelectric strips integrally bonding to one end portion of the substrate was produced. The dicing was performed with blades (Z09-SD4000-Y1-90: 72×0.05A1×40, Z09-SD4000-Y1-90: 72×0.025A1×40) rotated at 30,000 rpm and moved at 5 mm/sec. The width (the length in the Y direction and Z direction) and height (the length in the X direction) of each piezoelectric strip in the diced substrate were 50 μm and 4.5 mm, respectively. The width of grooving in the dicing was 25 μm.

Subsequently, the diced substrate was etched. The etching was in four cycles. First, Pure Etch PT303 (manufactured by Hayashi Pure Chemical Ind., Ltd.) was prepared as an etching solution for first etching. Then, 10 mL of the etching solution was placed in a glass Petri dish together with a stirring bar, and the etching solution was stirred by using a magnetic stirrer at a speed of 150 rpm. The temperature of etching solution 1 was 30° C. Next, the diced substrate was soaked in the etching solution for 40 minutes for first etching. Then, the diced substrate was soaked in hot water at a temperature of 80° C. for 40 minutes. Subsequently, the diced substrate was soaked in water at a temperature of 30° C., for which ultrasonic washing was performed at a frequency of 45 kHz for 10 seconds.

Then, 10 mL of the etching solution placed in a glass Petri dish was newly prepared as an etching solution for second etching by using the same procedure. The temperature of this etching solution was 30° C. Next, the diced substrate was soaked in the etching solution for 55 minutes. Then, the diced substrate was soaked in hot water at a temperature of 80° C. for 35 minutes for second etching. Subsequently, the diced substrate was soaked in water at a temperature of 30° C., for which ultrasonic washing was performed at a frequency of 45 kHz for 10 seconds.

Then, 10 mL of the etching solution placed in a glass Petri dish was newly prepared as an etching solution for third etching by using the same procedure. The temperature of this etching solution was 30° C. Then, the diced substrate was soaked in the etching solution for 65 minutes for third etching.

Then, 10 mL of the etching solution placed in a glass Petri dish was newly prepared as an etching solution for fourth etching by using the same procedure. The temperature of this etching solution was 38° C. Next, the diced substrate was soaked in the etching solution for 14 hours for fourth etching. Then, the diced substrate was soaked in hot water at a temperature of 80° C. for 30 minutes. Subsequently, the diced substrate was soaked in water at a temperature of 30° C., for which ultrasonic washing was performed at a frequency of 45 kHz for 10 seconds.

Thus, an etched substrate in which the width of each piezoelectric strip was 20 μm was produced.

Subsequently, the following components in the specified quantities were mixed together to prepare crosslinkable epoxy resin composition 1.

Elastomer epoxy resin 1: 95 parts by weight
Trifunctional or higher-functional epoxy resin 1: 5 parts by weight
Crosslinking agent 1: 12 parts by weight ALBIDUR EP2240 A (difunctional, manufactured by Evonik Industries AG: "ALBIDUR" is a registered trademark possessed by the manufacturer) was used for elastomer epoxy resin 1, TEPIC-VL (trifunctional, manufactured by Nissan Chemical Industries, Ltd., "TEPIC" is a registered trademark possessed by the manufacturer) was used for trifunctional or higher-functional epoxy resin 1, and ST12 (divalent, manufactured by Mitsubishi Chemical Corporation) was used for crosslinking agent 1.

Subsequently, crosslinkable epoxy resin composition 1 prepared was fed to the gaps of the plurality of piezoelectric strips in the etched substrate to fill the gaps with crosslinkable epoxy resin composition 1. Next, the etched substrate was left to stand at room temperature for 12 hours, and then left to stand under an environment at 50° C. for 3 hours to form a reaction product of crosslinkable epoxy resin composition 1. The interval between adjacent piezoelectrics in the Z direction and Y direction was then 2 μm.

Subsequently, the etched substrate was cut in the YZ plane to remove a portion not constituting a piezoelectric composite including the piezoelectric strips and the reaction products alternately disposed in alignment. Thereby, a piezoelectric composite including piezoelectrics and resins alternately disposed was obtained.

Next, each end surface of the piezoelectric composite in the X direction was polished by using the polisher MA-200e manufactured by Musashino Denshi K.K. and 9 µm abrasive grains to adjust the height (the length in the X direction) of the piezoelectric composite to 150 µm. Subsequently, the piezoelectric composite was polished by using 3 µm abrasive grains to adjust the height (the length in the X direction) of the piezoelectric composite to 130 µm. Then, the piezoelectric composite was polished by using 0.5 µm abrasive grains to adjust the height (the length in the X direction) of the piezoelectric composite to 120 µm and adjust the surface roughness of each end surface.

Subsequently, an electrode pair was formed on the end surfaces of the piezoelectric composite in the X direction through sputtering. The electrode pair was composed of a chromium layer having a thickness of 50 nm and disposed in the piezoelectric composite side and a gold layer having a thickness of 200 nm and disposed on the chromium layer. Thus, piezoelectric element 1 was produced through the above procedure.

[Production of Piezoelectric Element 2]

Piezoelectric element 2 was produced in the same manner as for piezoelectric element 1 except that the etching duration in the third etching was changed to 90 minutes, the etching duration in the fourth etching was changed to 21 hours, trifunctional or higher-functional epoxy resin 2 was used in place of trifunctional or higher-functional epoxy resin 1, and the content of crosslinking agent 1 was changed as shown in Table 1. TEPIC-L (manufactured by Nissan Chemical Industries, Ltd., "TEPIC" is a registered trademark possessed by the manufacturer) was additionally used as trifunctional or higher-functional epoxy resin 2.

[Production of Piezoelectric Elements 3 to 13]

Piezoelectric elements 3 to 13 were produced in the same manner as for piezoelectric element 2 except that the components of the crosslinkable epoxy resin composition were changed as shown in Table 1.

JER828 (difunctional, manufactured by Mitsubishi Chemical Corporation) was used as a difunctional or monofunctional epoxy resin.

ALBIFLEX 296 (difunctional, manufactured by Evonik Industries AG, "ALBIFLEX" is a registered trademark) was used for elastomer epoxy resin 2, Kane Ace MX-217 (trifunctional or higher-functional, manufactured by KANEKA CORPORATION, "Kane Ace" is a registered trademark possessed by the manufacturer) was used for elastomer epoxy resin 3, and Kane Ace MX-451 (trifunctional, manufactured by KANEKA CORPORATION, "Kane Ace" is a registered trademark possessed by the manufacturer) was used for elastomer epoxy resin 4.

TEPIC-UC (hexafunctional, manufactured by Nissan Chemical Industries, Ltd., "TEPIC" is a registered trademark possessed by the manufacturer) was used for trifunctional or higher-functional epoxy resin 3, and EPICLON EXA-4700 (tetrafunctional, manufactured by DIC Corporation, "EPICLON" is a registered trademark possessed by the manufacturer) was used for trifunctional or higher-functional epoxy resin 4.

KarenzMT PE1 (tetravalent, manufactured by Showa Denko K.K., "KarenzMT" is a registered trademark possessed by the manufacturer) was used for crosslinking agent 2, methylhimic anhydride (MHAC-P, divalent, manufactured by Hitachi Chemical Co., Ltd.) was used for crosslinking agent 3, and RIKACID MTA-15 (tetravalent, manufactured by New Japan Chemical Co., Ltd., "RIKACID" is a registered trademark possessed by the manufacturer) was used for crosslinking agent 4.

As a crosslinking accelerator, 2,4,6-tris(dimethylaminomethyl)phenol (TAP, manufactured by Tokyo Chemical Industry Co., Ltd.) was used.

As an additive (metal alkoxide compound), bis[3-(triethoxysilyepropyl] tetrasulfide (C-1, manufactured by Wako Pure Chemical Industries, Ltd.) was used.

[Production of Piezoelectric Element C1]

Only the electrode pair was formed on a PMN-PT substrate having a size of 5 mm×5 mm and a thickness of 0.12 mm, without performing any of dicing, etching, and filling with the crosslinkable epoxy resin composition, to produce piezoelectric element C1.

[Production of Piezoelectric Element C2]

A diced substrate for piezoelectric element C2 was obtained in the same manner as for the diced substrate for piezoelectric element 1 except that a PMN-PT substrate (manufactured by JFE MINERAL COMPANY, LTD.) with a size of 20 mm×20 mm and a thickness of 300 µm was prepared and dicing was performed so that the width and height of each piezoelectric strip in the diced substrate reached 80 µm and 250 µm, respectively, and the width of grooving in dicing reached 20 µm. Subsequently, piezoelectric element C2 was produced in the same manner as for piezoelectric element 1 except that etching was not performed for the diced substrate after dicing, and the components of the crosslinkable epoxy resin composition were changed as shown in Table 1.

[Production of Piezoelectric Element C3]

Piezoelectric element C3 was produced in the same manner as for piezoelectric element 2 except that the etched substrate was soaked in a dispersion prepared by dispersing 0.1 g of Micropearl SP (particle size: 10 µm, manufactured by SEKISUI CHEMICAL CO., LTD.) in 200 mL of water to allow gap-controlling particles to attach to the surface of the etched substrate, and the components of the crosslinkable epoxy resin composition were changed as shown in Table 1.

[Production of Piezoelectric Element C4]

Piezoelectric element C4 was produced in the same manner as for piezoelectric element 2 except that the components of the crosslinkable epoxy resin composition were changed as shown in Table 1.

[Production of Piezoelectric Element C5]

Piezoelectric element C5 was produced in the same manner as for piezoelectric element C4 except that the components of the crosslinkable epoxy resin composition were changed as shown in Table 1.

Table 1 shows the piezoelectric element No.; the width of each piezoelectric (the length in the Y direction and X direction); the interval of the piezoelectrics (the width of the reaction product); the aspect ratio of each piezoelectric; the type, content, and number of epoxy groups per molecule of the crosslinkable epoxy resin; the type, content, and number of crosslinkable functional groups (crosslinking value) of the crosslinking agent; the type and content of the crosslinking accelerator; and the type and content of the additive. In Table 1, "aspect ratio" refers to a ratio of the height (the length in the X direction) to the width in each piezoelectric. In Table 1, "AR" denotes the aspect ratio of each piezoelectric, "m" denotes the number of functional groups of the crosslinkable epoxy resin, and "n" denotes the crosslinking value of the crosslinking agent. With respect to the type of the crosslinkable epoxy resin, "A" indicates difunctional or monofunctional crosslinkable epoxy resin, "B" indicates crosslinkable elastomer epoxy resin, and "C" indicates trifunctional or higher-functional crosslinkable epoxy resin.

composite and the electrode) was measured by using the digital force gauge ZP-20N (manufactured by IMADA CO.,

TABLE 1

| Piezo-electric element No. | Piezoelectric Width [μm] | Piezoelectric Interval [μm] | Piezoelectric AR [-] | Crosslinkable epoxy resin A Content [part by weight] | A m | B No. | B Content [part by weight] | B m | C No. | C Content [part by weight] | C m | Crosslinking agent No. | Crosslinking agent Content [part by weight] | n | Accelerator Content [part by weight] | Additive Content [part by weight] |
|---|---|---|---|---|---|---|---|---|---|---|---|---|---|---|---|---|
| 1  | 20   | 2  | 6     | —   | — | 1 | 95  | 2          | 1 | 5 | 3 | 1 | 32 | 2 | —   | —   |
| 2  | 10   | 2  | 12    | —   | — | 1 | 95  | 2          | 2 | 5 | 3 | 1 | 34 | 2 | —   | —   |
| 3  | 10   | 2  | 12    | 65  | 2 | 2 | 30  | 2          | 2 | 5 | 3 | 1 | 36 | 2 | —   | —   |
| 4  | 10   | 2  | 12    | —   | — | 1 | 95  | 2          | 3 | 5 | 6 | 1 | 32 | 2 | —   | —   |
| 5  | 10   | 2  | 12    | —   | — | 3 | 100 | 3 or higher| — | — | — | 1 | 40 | 2 | —   | —   |
| 6  | 10   | 2  | 12    | —   | — | 4 | 100 | 3          | — | — | — | 1 | 76 | 2 | —   | —   |
| 7  | 10   | 2  | 12    | —   | — | 1 | 97  | 2          | 4 | 3 | 4 | 1 | 30 | 2 | —   | —   |
| 8  | 10   | 2  | 12    | —   | — | 1 | 100 | 2          | — | — | — | 2 | 70 | 4 | 5   | —   |
| 9  | 10   | 2  | 12    | —   | — | 3 | 100 | 3 or higher| — | — | — | 1 | 40 | 2 | —   | 1.5 |
| 10 | 10   | 2  | 12    | —   | — | 1 | 95  | 2          | 3 | 5 | 3 | 3 | 60 | 2 | —   | —   |
| 11 | 10   | 2  | 12    | —   | — | 1 | 95  | 2          | 3 | 5 | 3 | 4 | 60 | 4 | —   | —   |
| 12 | 10   | 2  | 12    | —   | — | 1 | 97  | 2          | 4 | 3 | 3 | 3 | 60 | 2 | —   | —   |
| 13 | 10   | 2  | 12    | —   | — | 3 | 100 | 3 or higher| — | — | — | 2 | 70 | 4 | 5   | —   |
| C1 | 5000 | —  | 0.024 | —   | — | — | —   | —          | — | — | — | — | —  | — | —   | —   |
| C2 | 80   | 20 | 1.5   | 100 | 2 | — | —   | —          | — | — | — | 1 | 50 | 2 | —   | —   |
| C3 | 10   | 10 | 12    | 100 | 2 | — | —   | —          | — | — | — | 1 | 50 | 2 | —   | —   |
| C4 | 10   | 2  | 12    | 100 | 2 | — | —   | —          | — | — | — | 1 | 50 | 2 | —   | —   |
| C5 | 10   | 2  | 12    | —   | — | 1 | 100 | 2          | — | — | — | 1 | 32 | 2 | —   | —   |

[Evaluation]

(Processability)

In polishing for the end surfaces of the piezoelectric composite in the production process for each piezoelectric element, polishing was performed in a manner such that a stress of 98.1 kPa was applied to the piezoelectric composite. Subsequently, the piezoelectric composite after polishing was observed by using an electron microscope. One hundred piezoelectrics were observed for generation of peeling-off of the piezoelectric and reaction product and generation of cracks of the piezoelectric. The processability of the piezoelectric composite was evaluated by using the criteria below. Ratings of A and B were determined to be acceptable.

(Evaluation Criteria)

A: the total number of peeling-off and cracks as mentioned above was one or less.

B: the total number of peeling-off and cracks as mentioned above was two or more and less than five.

C: the total number of peeling-off and cracks as mentioned above was five or more.

D: peeling-off as mentioned above was significant, and the processability was out of evaluation.

(Adhesion)

For each piezoelectric element, a Capton tape (manufactured by Nitto Denko Corporation, "Capton" is a registered trademark possessed by E. I. du Pont de Nemours and Company) having a width of 8 mm was pressure-bonded onto one electrode for reinforcement, and an epoxy adhesive was applied onto the other electrode. The piezoelectric element and a glass substrate were pressure-bonded by using a pressure jig at a pressure of 15×10⁵ Pa in a manner such that the other electrode coated with the epoxy adhesive and the glass substrate were brought into contact. Subsequently, the epoxy adhesive was cured under an environment at 50° C. Then, one electrode was peeled off together with the Capton tape. In this peeling, force required to peel off the electrode (the adhesion force between the piezoelectric composite and the electrode) was measured by using the digital force gauge ZP-20N (manufactured by IMADA CO., LTD.), and the adhesion force was evaluated by using the criteria below. Ratings of A and B were determined to be acceptable.

(Evaluation criteria)

A: 5 N or higher

B: 4 N or higher and lower than 5 N

C: 3 N or higher and lower than 4 N

D: lower than 3 N (Electromechanical Coupling Factor)

For each piezoelectric element, the electromechanical coupling factor, $k_t$, was measured in accordance with a resonance-antiresonance method with an impedance analyzer (Agilent 4294A; manufactured by Agilent Technologies, Inc.). A case that $k_t$ was 0.75 or higher was determined to be acceptable.

(Durability)

Oleic acid and 5 mass % glutaraldehyde aqueous solution were prepared as test solutions. Each piezoelectric element processed into a width of 1 mm (as a length in the X direction and Z direction) was soaked in each test solution adjusted to 40° C. for 24 hours. The change rate of the mass of the reaction product between before and after soaking of the piezoelectric element in each test solution was measured. The change rate was calculated by using the equation below. The durability was evaluated on the basis of the evaluation criteria shown in Table 2. Ratings of A and B were determined to be acceptable:

$$\text{Change rate} = (w_a - w_b) / \{w_b \times (1 - X^2)\}$$

$$X = a/(a+b)$$

wherein, $w_a$ denotes the mass of the piezoelectric element after soaking; $w_b$ denotes the mass of the piezoelectric element after soaking; a denotes the width of each piezoelectric; and b denotes the interval of the piezoelectrics.

TABLE 2

| Change rate | | 5mass % glutaraldehyde aqueous solution | | |
|---|---|---|---|---|
| | | Less than 1% | 1% or more and less than 50% | 50% or more |
| oleic acid | Less than 1% | A | B | C |
| | 1% or more and less than 50% | B | C | D |
| | 50% or more | C | D | D |

Table 3 shows piezoelectric element Nos. and the evaluation results for the processability, adhesion, electromechanical coupling factor, $k_t$, and durability.

TABLE 3

| Piezoelectric element No. | Processability | Adhesion | Kt | Durability |
|---|---|---|---|---|
| 1 | B | B | 0.78 | B |
| 2 | B | B | 0.80 | A |
| 3 | B | B | 0.81 | B |
| 4 | A | A | 0.80 | A |
| 5 | B | B | 0.79 | A |
| 6 | A | B | 0.78 | A |
| 7 | B | B | 0.81 | A |
| 8 | A | A | 0.82 | A |
| 9 | A | A | 0.81 | A |
| 10 | A | A | 0.82 | A |
| 11 | A | A | 0.81 | A |
| 12 | A | A | 0.80 | A |
| 13 | A | A | 0.82 | A |
| C1 | A | D | 0.58 | A |
| C2 | B | C | 0.70 | C |
| C3 | C | C | 0.79 | C |
| C4 | C | C | 0.72 | C |
| C5 | D | — | — | — |

As is clear from Table 3, the processability, adhesion, electromechanical coupling factor, $k_t$, and durability were sufficient in the cases of piezoelectric elements 1 to 13. This is probably because the reaction product is a reaction product of a crosslinkable epoxy resin composition containing an elastomer component, a crosslinkable epoxy resin, and a crosslinking agent, and one or each of the number of epoxy groups possessed by the crosslinkable epoxy resin per molecule and the crosslinking value of the crosslinking agent is 3 or more.

In contrast, at least one of the processability, adhesion, electromechanical coupling factor, $k_t$, and durability was insufficient in the cases of piezoelectric elements C1 to C5. This is probably because each of piezoelectric elements C1 to C5 does not include the reaction product in which one or each of the number of epoxy groups possessed by the crosslinkable epoxy resin per molecule and the crosslinking value of the crosslinking agent is 3 or more. For piezoelectric element C5, excessive peeling-off of the reaction product and piezoelectric took place in polishing the end surfaces of the piezoelectric composite, and evaluation of the adhesion, electromechanical coupling factor, and durability failed.

INDUSTRIAL APPLICABILITY

One or more embodiments of the present invention enable formation of an ultrasound probe having high sensitivity to ultrasound. Accordingly, one or more embodiments of the present invention are expected to contribute to further widespread use of ultrasound imaging apparatuses.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A piezoelectric element comprising:
    a piezoelectric composite; and
    an electrode pair that is disposed to face each other with the piezoelectric composite sandwiched therebetween and applies a voltage to the piezoelectric composite, wherein
    the piezoelectric composite comprises:
        a plurality of piezoelectrics disposed in alignment along a direction perpendicular to a facing direction of the electrode pair at an interval of 1 to 10 μm, wherein a ratio of a length in the facing direction to a length in an alignment direction in each of the piezoelectrics is 5 or higher; and
        a reaction product of a crosslinkable epoxy resin composition containing an elastomer component, a crosslinkable epoxy resin, and a crosslinking agent, wherein the reaction product fills a gap of the plurality of piezoelectrics, and
    one or each of a number of epoxy groups possessed by the crosslinkable epoxy resin per molecule and a crosslinking value of the crosslinking agent is 3 or more.

2. The piezoelectric element according to claim 1, wherein the electrode pair is disposed on both end surfaces of each of the piezoelectrics and both end surfaces of the reaction product.

3. The piezoelectric element according to claim 1, wherein the elastomer component is an elastomer particle having a number average primary particle size of 1 μm or smaller.

4. The piezoelectric element according to claim 3, wherein the elastomer component is silicone elastomer.

5. The piezoelectric element according to claim 1, wherein
    the crosslinkable epoxy resin contains a trifunctional or higher-functional crosslinkable epoxy resin, and
    the trifunctional or higher-functional crosslinkable epoxy resin includes a constitutional unit having an epoxy group.

6. The piezoelectric element according to claim 1, wherein
    the crosslinkable epoxy resin contains a trifunctional or higher-functional crosslinkable epoxy resin, and
    the trifunctional or higher-functional crosslinkable epoxy resin includes no constitutional unit.

7. The piezoelectric element according to claim 1, wherein the crosslinkable epoxy resin has an aromatic ring in its molecular structure.

8. The piezoelectric element according to claim 1, wherein
    the crosslinking agent has a thiol group, and
    the reaction product and each of the piezoelectrics are bonded together via a sulfur atom of the thiol group.

9. The piezoelectric element according to claim 1, wherein
    the crosslinkable epoxy resin composition further contains a metal alkoxide compound, and
    the reaction product and each of the piezoelectrics are bonded together via a residue of the metal alkoxide compound.

10. An ultrasound probe comprising the piezoelectric element according to claim 1.

11. An ultrasound imaging apparatus comprising the ultrasound probe according to claim 10.

12. A method for producing a piezoelectric element, the method comprising:
- filling a gap of a plurality of piezoelectrics disposed in alignment at an interval of 1 to 10 μm, wherein a ratio of a length in a height direction intersecting a plane lying along an alignment direction to a length in the alignment direction in each of the piezoelectrics is 5 or higher, with a crosslinkable epoxy resin composition containing an elastomer component, a crosslinkable epoxy resin, and a crosslinking agent, wherein one or each of a number of epoxy groups possessed by the crosslinkable epoxy resin per molecule and a crosslinking value of the crosslinking agent is 3 or more;
- obtaining a piezoelectric composite through reacting an epoxy group of the crosslinkable epoxy resin and a crosslinkable functional group of the crosslinking agent to form a reaction product of the crosslinkable epoxy resin composition; and
- forming an electrode pair on both end surfaces of the piezoelectric composite in the height direction, wherein the electrode pair is disposed to face each other and applies a voltage to the piezoelectric composite.

* * * * *